US006509165B1

(12) United States Patent
Griffin et al.

(10) Patent No.: US 6,509,165 B1
(45) Date of Patent: *Jan. 21, 2003

(54) DETECTION METHODS FOR TYPE I DIABETES

(75) Inventors: Ann C. Griffin, Hanover, NH (US); William F. Hickey, Lyme, NH (US)

(73) Assignee: Trustees of Dartmouth College, Hanover, NH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/472,701

(22) Filed: Jun. 6, 1995

Related U.S. Application Data

(63) Continuation-in-part of application No. 08/272,220, filed on Jul. 8, 1994, now abandoned.

(51) Int. Cl.[7] .............................................. G01N 33/53
(52) U.S. Cl. ........................... 435/7.24; 435/7.1; 435/6; 435/29; 424/198.1; 436/506; 530/806; 530/868
(58) Field of Search ................................ 435/7.1, 7.24, 435/6, 4, 29; 424/198.1; 436/506; 530/806, 868

(56) References Cited

U.S. PATENT DOCUMENTS 5,130,297 A    7/1992   Sharma et al.

FOREIGN PATENT DOCUMENTS

| WO | WO90/10449 | 9/1990 |
| WO | WO91/17186 | 11/1991 |
| WO | WO 92/02543 | 2/1992 |
| WO | WO92/03733 | 3/1992 |
| WO | WO 92/07952 | 5/1992 |
| WO | WO 92/16234 | 10/1992 |
| WO | WO 92/18150 | 10/1992 |

OTHER PUBLICATIONS

Jorgensen et al. in Ann. Rev. Immunol. p. 835–843, 1992.*
Janeway et al. Immuno Biology 11:24–11:26, 1994.*
Lin, R–W et al. J. Exp. Med. 173:1433–1439. Jun. 1991.*
Madsen, OD et al. Diabetologia 29(2):115–118, Feb. 1986.*
Keller, RJ. J. Autoimmunity 3(3):321–327, Jun. 1990.*
Palmer et al Prediction and Prevention of IDDM–1991. Diabetes Aug. 1991 vol. 40 pp. 943–947.*
Eisenbarth Immune Mechanisms of Beta Cell Destruction in the Prediabetic Phase of IDDM Patients: Research Methodologies Identifying Susceptible Individuals. In Research Methodologies in Human Disease Part 1. Edited by Mogensen and Small Berlin 1994 p 89–104.*
Kuglin et al Evidence of IgG Autoantibodies Against Human Proinsulin in Patients with IDDM Before Insulin Treatment. Diabetes Jan. 1988 p. 130–132.*

Rudy et al Similar Peptides from Two B Cell Autoantigens, Proinsulin and Glutamic Acid Decarboxylase, Stimulate T Cells of Individuals at Risk for Insulin–Dependent Diabetes. Molecular Medicine Sep. 1995 p. 625–633.*
Becker and Federlin, "Autoantigene beim Typ–I–Diabetes," *Immunität und Infektion*, 19:6, 167–169 (1991); English Abstract Only.
Crowther et al., "Epitope analysis of human insulin and intact proinsulin," *Protein Eng.*, 7:1, 137–144 (1994).
Föhles et al., "Human proinsulin. V. Synthesis of a protected peptide fragment corresponding to the sequence 24–45 of the prohormone," *Hoppe–Seyler's Z. Physiol. Chem.*, 361:6, 849–856 (1980).
Naithani et al., "Progress in the chemical synthesis of human proinsulin in Aachen," Int. Congr. Ser.—*Excerpta Med.*, vol. date 1978, 468, 36–40 (1978).
Palmer et al., "Insulin Antibodies in Insulin–Dependent Diabetics Before Insulin Treatment," *Science*, 222:4630, 1337–1339 (1983).
Yanaihara et al., "Synthesis of C–peptides and human proinsulin," *Diabetes*, 27, supp. 1, 149–160 (1978).
Yanaihara et al., "Synthetic C–peptides and proinsulin synthesis," Int. Cong. Ser.—*Excerpta Med.*, 413, 116–125 (1977).
Adorini, (1992) "Selective Suppression of T–Cell Activation by Administration of MHC Class II–Binding Peptides," *Transplantation Proceedings*, vol. 24, No. 4, Suppl. 2, pp. 14–16.
Bell, et al., (1979) "Nucleotide sequence of a cDNA clone encoding human preproinsulin," *Nature*, vol. 282, p. 525–527.
Bodmer, H., et al., (1994) "Diversity of Endogenous Epitopes Bound to MHC Class II Molecules Limited by Invariant Chain", *Science*, vol. 263, pp. 1284–1286.
Charron, D.J., (1992) "New aspects of HLA: perspectives for rheumatoid arthritis", *Clinical and Experimental Rheumatology*, vol. 10, pp. 293–296.

(List continued on next page.)

Primary Examiner—Patrick J. Nolan
Assistant Examiner—Gerald R. Ewoldt
(74) *Attorney, Agent, or Firm*—Seed Intellectual Property Law Group PLLC

(57) ABSTRACT

Proinsulin peptide compounds that modulate an immunological response by T cells of Type I diabetic subjects are disclosed. The proinsulin peptide compounds of the invention are preferably derived from a region of proinsulin that spans the junction between the B chain and C peptide of proinsulin. Pharmaceutical compositions comprising the proinsulin peptide compounds are also disclosed. An immunological response to a proinsulin peptide compound of the invention can be used as an indicator of Type I diabetes in a subject. Accordingly, the invention provides diagnostic assays for Type I diabetes using the proinsulin peptide compounds. Methods for inhibiting the development or progression of Type I diabetes in a subject by administering a proinsulin peptide compound are also disclosed.

1 Claim, 3 Drawing Sheets

OTHER PUBLICATIONS

Daniel, et al., (1995) "Epitope specificity, cytokine production profile and diabetogenic activity of insulin–specific T cell clones isolated from NOD mice," *Eur. J. Immunol.*, vol. 25, pp. 1056–1062.

Delovitch, et al., (1988) "Pathways of Processing of Insulin by Antigen–Presenting Cells," *Immunological Reviews*, vol. 106, pp. 195–222.

Gianani, et al., (1994) "Prediction and prevention of type 1 diabetes," *J. Endocrinol. Invest.*, vol. 17, pp. 533–543.

Griffin, A. and Hickey, W., (1994) "Development of Insulitis in Rats Following Transfer of T Cells Specific for a MHC–Class II Restricted Peptide Fragment of Proinsulin", *The FASEB Journal*, vol. 8, No. 5, Abstract # 5483.

Guéry, et al., (1992) "Selective Immunosuppression by Administration of Major Histocompatibility Complex (MHC) Class II–binding Peptides. I. Evidence for In Vivo MHC Blockade Preventing T Cell Activation," *J. Exp. Med.*, vol. 175, pp. 1345–1352.

Guéry, et al., (1993) "Selective Immunosuppression by Administration of Major Histocompatibility Complex Class II–binding Peptides. II. Preventive Inhibition of Primary and Secondary In Vivo Antibody Responses," *J. Exp. Med.*, vol. 177, pp. 1461–1468.

Halban, (1991) "Structural domains and molecular lifestyles of insulin and its precursors in the pancreatic Beta cell," *Diabetologia*, vol. 34, pp. 767–778.

Hartling, et al., (1989) "Elevated Proinsulin in Healthy Siblings of IDDM Patients Independent of HLA Identity," *Diabetes*, vol. 38, pp. 1271–1274.

Heaton, et al., (1988) "Increased proinsulin levels as an early indicator of B–cell dysfunction in non–diabetic twins of Type 1 (insulin–dependent) diabetic patients," *Diabetologia*, vol. 31, pp. 182–184.

Hurtenbach, et al., (1993) "Prevention of Autoimmune Diabetes in Non–Obese Diabetic Mice by Treatment with a Class II Major Histocompatibility Complex–blocking Peptide," *J. Exp. Med.*, vol. 177, pp. 1499–1504.

Long, E.O., et al., (1983) "Isolation of cDNA clones for the p33 invariant chain associated with HLA–DR antigens", *Proceedings of the National Academy of Sciences*, vol. 80, pp. 5714–5718.

Maryanski, J.L., et al., (1990) "Competitor Analogs for Defined T Cell Antigens: Peptides Incorporating a Putative Binding Motif and Polyproline or Polyglycine Spacers", *Cell*, vol. 60, No. 1, pp. 63–72.

McKnight, A., et al., (1989) "Sequence of a rat MHC class II–associated invariant chain cDNA clone containing a 64 amino acid thyroglobulin–like domain" *Nucleic Acid Research*, vol. 17, No. 10, pp. 3983–3984.

Momburg, F., et al., (1993) "Epitope–specific Enhancement of Antigen Presentation by Invariant Chain", *J. Exp. Med.*, vol. 178, pp. 1453–1458.

Naquet, et al., (1987) "Processing and Presentation of Insulin," *The Journal of Immunology*, vol. 139, No. 12, pp. 3955–3963.

Naquet, et al., (1988) "T Cell Autoreactivity to Insulin in Diabetic and Related Non–diabetic Individuals," *The Journal of Immunology*, vol. 140, No. 8, pp. 2569–2578.

Naquet, et al., (1989) "Sulfated Beef Insulin Treatment Elicits CD8+ T Cells That May Abrogate Immunologic Insulin Resistance in Type I Diabetes," *J. Clin. Invest.*, vol. 84, pp. 1479–1487.

Posselt, et al., (1992) "Prevention of Autoimmune Diabetes in the BB Rat by Intrathymic Islet Transplantation at Birth," *Science*, vol. 256, pp. 1321–1324.

Pugliese, et al., (1994) "The Paternally Inherited Insulin Gene B Allele (1,428 FokI site) Confers Protection from Insulin–dependent Diabetes in Families," *Journal of Autoimmunity*, vol. 7, pp. 687–694.

Rath, et al., (1992) "T and B cell receptors discriminate major histocompatibility complex class II conformations influenced by the invariant chain," *Eur. J. Immunol.*, vol. 22, pp. 2121–2127.

Robbins, et al., (1984) "Biologic and Clinical Importance of Proinsulin," *The New England Journal of Medicine*, vol. 310, No. 18, pp. 1165–1168.

Roche, P.A., et al., (1992) "Stable surface expression of invariant chain prevents peptide presentation by HLA–DR", *The EMBO Journal*, vol. 11, No. 8, pp. 2841–2847.

Sakai, et al., (1989) "Prevention of experimental encephalomyelitis with peptides that block interaction of T cells with major histocompatibility complex proteins," *Proc. Natl. Acad. Sci. USA*, vol. 86, pp. 9470–9474.

Smilek, et al. (1991) "A single amino acid change in a myelin basic protein peptide confers the capacity to prevent rather than induce experimental autoimmune encephalomyelitis," *Proc. Natl. Acad. Sci. USA*, vol. 88, pp. 8633–9637.

Smith, et al., (1992) "Expression of myosin–class II major histocompatibility complexes in the normal myocardium occurs before induction of autoimmune myocarditis," *Proc. Natl. Acad. Sci. USA*, vol. 89, pp. 9131–9135.

Spinas, et al., (1992) "Elevated proinsulin Levels Related to Islet Cell Antibodies in First–Degree Relatives of IDDM Patients," *Diabetes Care*, vol. 15, No. 5, pp. 632–637.

Strubin, M., et al., (1986) "Alternative splicing and alternative initiation of translation explain the four forms of the Ia antigen–associated invariant chain", *The EMBO Journal*, vol. 5, No. 13, pp. 3483–3488.

Strubin, M., et al., (1984) "The complete sequence of the mRNA for the HLA–DR–associated invariant chain reveals a polypeptide with an unusual transmembrane polarity", *The EMBO Journal*, vol. 3, No. 4, pp. 869–872.

Sures, et al., (1980) "Nucleotide Sequence of Human Preproinsulin Complementary DNA," *Science*, vol. 208, pp. 57–59.

Teyton, L., et al., (1990) "Invariant chain distinguishes between the exogenous and endogenous antigen presentation pathways", *Nature*, vol. 348, pp. 39–44.

Valli, et al., (1993) "Binding of Myelin Basic Protein Peptides to Human Histocompatibility Leukocyte Antigen Class II Molecules and Their Recognition by T Cells from Multiple Sclerosis Patients," *J. Clin. Invest.*, vol. 91, pp. 616–628.

Viville, S., et al., (1993) "Mice Lacking the MHC Class II–Associated Invariant Chain", *Cell*, vol. 72, pp. 635–648.

Wauben, M.H.M., et al., (1992) "Disease Inhibition by Major Histocompatability Complex Binding Peptide Analogues of Disease–associated Epitopes: More than Blocking Alone", *J. Exp. Med.*, vol. 176, pp. 667–677.

Wegmann, et al., (1994) "Insulin–specific T cells are a predominant component of islet infiltrates in pre–diabetic NOD mice," *Eur. J. Immunol.*, vol. 24, pp. 1853–1857.

Wegmann, et al., (1994) "Analysis of the Spontaneous T Cell Response to Insulin in NOD mice," *Journal of Autoimmunity*, vol. 7, pp. 833–843.

Wraith, et al., (1989) "Antigen Recognition in Autoimmune Encephalomyelitis and the Potential for Peptide–Mediated Immunotherapy," *Cell*, vol. 59, pp. 247–255.

Yu, et al., (1994) "Quantitation of Glutamic Acid Decarboxylase Autoantibody Levels in Prospectively Evaluated Relatives of Patients With Type I Diabetes," *Diabetes*, vol. 43, pp. 1229–1233.

* cited by examiner

DETECTION METHODS FOR TYPE I DIABETES

RELATED APPLICATION

This application is a continuation-in-part of U.S. patent application Ser. No. 08/272,220, filed Jul. 8, 1994, now abandoned, the entire contents of which are incorporated by reference.

GOVERNMENT FUNDING

Work described herein was supported at least in part under grants RO1-NS-27321 and T32-AI07363 awarded by the National Institutes of Health. The U.S. government therefore may have certain rights in this invention.

BACKGROUND OF THE INVENTION

Type I, or insulin-dependent, diabetes mellitus (also referred to herein as DM-I) is known to occur spontaneously in humans, rats and mice (Castaño, L and Eisenbarth, G. (1990) *Ann. Rev. Immunol.* 8:647–679). There is a genetic susceptibility to DM-I associated with certain haplotypes of Class II antigens of the major histocompatability complex (MHC), i.e., HLA-DR3, -DR4 and -DQ3.2 in humans (see e.g., Platz. P. et al. (1981) *Diabetologia* 21:108–115; Todd, J. et al. (1987) *Nature* 329:599–604); RT1$^u$ in Bio-Breeding (BB) rats (see e.g., Colle, E. (1990) *Clin. Immunol. & Immunopathol.* 57:1–9; Parfrey, N. A. et al. (1989) *Crit. Rev. Immunol.* 9:45–65) and H-2$^{g7}$ in non-obese diabetic (NOD) mice (see e.g., Kikutani, H. and Makino, S. in *Adv. Immunol.* (Dixon, F. J., ed.), pp. 285–323, New York, N.Y.: Academic Press, Inc., 1992). The pathology of DM-I consists of the progressive inflammatory infiltration of pancreatic islets (i.e., insulitis) containing immunocytes targeted specifically to insulin-secreting β-cells (see e.g., Bottazzo, G. F. et al. (1985) *N. Eng. J. Med.* 313:353–360; Foulis, A. K. et al. (1991) *J. Pathol.* 165:97–103; Hanenberg, H. et al. (1991) *Diabetologia* 32:126–134). This pathology develops over an indeterminate period of time (months to years).

It has become clear that the development of Type I diabetes occurs as a result of a complex relationship involving genetic predisposition, environmental influences, and additional undefined co-factors. In attempting to understand the pathogenesis of DM-I, the most elusive pieces of information have been the definition of the inciting autoantigen (s), and whether cellular or humoral-mediated autoreactivity is the primary event. Serum autoantibodies directed against islet cell cytoplasm and surface antigens (i.e., ICA, ICSA), insulin (IA'A) and glutamic acid decarboxylase (GAD) can be found in pre-diabetic and newly diagnosed diabetic humans and animals (see e.g., Rowley, M. et al. (1992) *Diabetes* 41:548–551; Palmer, J. et al. (1983) *Science* 222:1337–9; MacLaren, N. et al. (1988) *Diabetes* 38:534–538; Baekkeskov, S. et al. (1990) *Nature* 347:151–156; Velleso, L. A. et al. (1993) *Diabetologia* 36:39–46). Unfortunately, correlations between antibody titers against these antigens and the clinical onset of diabetes have not been successfully predictive. In addition, a number of other β-cell antigens become exposed as islets are destroyed such as a 69kd islet cell autoantigen (ICA69) (Pietropaolo, M. et al. (1993) *J. Clin. Invest.* 92:359–371), 38kd and 62kd insulin secretory granule proteins (Roep, B. O. et al. (1991) *Lancet* 337:1439–1441; Brudzynski, K. et al. (1992) *J. Autoimm.* 5:453–463) and proislets (Harrison, L. C. et al. (1992) *J. Clin. Invest.* 89:1161–65; Harrison, L. et al. in *Advances in Endocrinology & Metabolism* (Mazzaferri, E. L. et al., ed.), pp. 35–94, St. Louis, Mo.: Mosby-Year Book, 1990). However, it is not clear whether the cellular and/or humoral immune responses to these antigens are the cause or simply a consequence of ongoing islet cell damage. In short, the immunologic nature of the pathogenic mechanism and the exact antigen(s) inducing the diabetogenic attack have yet to be elucidated.

Over one half million people in the United States suffer from insulin-dependent diabetes. Prior to 1921, people who developed DM-I were not expected to live much more than a year after diagnosis. Afflicted individuals suffered from clinical signs of chronic hyperglycemia (e.g., excessive thirst and urination, rapid weight loss) as a consequence of abnormal carbohydrate metabolism. Once insulin was purified and administered, the life-expectancy of diabetics increased dramatically. However, DM-I is a chronic disease that requires life-long treatment to prevent acute illness and to reduce the risk of long-term complications. Restrictive diets and daily insulin injections can be burdensome for patients, thus reducing compliance, and even with treatment complications such as cataracts, retinopathy, glaucoma, renal disease and circulatory disease are prevalent.

Accordingly, more effective treatments for Type I diabetes are needed, in particular therapies that address the autoimmune basis of the disease, rather than merely treating the symptoms. Additionally, given that the "pre-diabetic" phase of DM-I is long in duration and clinically asymptomatic, one important opportunity for therapeutic intervention falls during this period. However, effective diagnostic assays that can identify people in this pre-diabetic phase are lacking. Methods that would enable identification of early or mounting β-cell abnormalities in individuals predisposed to diabetes are needed and would allow treatment early in the disease process, which may help to avert life-long insulin dependence.

SUMMARY OF THE INVENTION

This invention pertains to proinsulin peptide compounds which modulate an immunological response by T cells of Type I diabetic subjects. In one embodiment, a proinsulin peptide compound of the invention stimulates an immunological response by the T cells. For example, humans with DM-I have greater numbers of circulating T cells which respond to a specific proinsulin peptide described herein than do non-diabetic control humans. Accordingly, a subject's immunological responsiveness to a stimulatory proinsulin peptide compound can be used as an indicator of DM-I. In another embodiment, a proinsulin peptide compound of the invention inhibits an immunological response by T cells of Type I diabetic subjects. The invention further provides therapeutic and preventative methods involving the use of the proinsulin peptide compounds of the invention to inhibit or prevent T cell responsiveness to proinsulin in Type I diabetic subjects.

In a preferred embodiment, the proinsulin peptide compound that modulates an immunological response from T cells of Type I diabetic subjects is derived from a region of proinsulin that spans the junction between the B chain and the C peptide of proinsulin. In another embodiment, the proinsulin peptide compound is a modified form of a proinsulin peptide derived from this region. Such modified forms include peptides that have amino acid substitutions compared to the native proinsulin amino acid sequence yet retain certain structural and functional features of the native peptide. Other modified forms of the proinsulin peptide compounds within the scope of the invention include peptides with end-terminal or side chain covalent modifications and peptide analogs and mimetics. Such modified proinsulin peptides can be selected for altered properties of the peptide, e.g., stability, solubility, immunogenicity, etc. The proinsulin peptide compounds of the invention can be incorporated into pharmaceutical compositions suitable for administration to a subject.

Another aspect of the invention pertain to a method for detecting an indicator of Type I diabetes in a subject by detecting an immunological activity against a proinsulin peptide compound of the invention in a biological sample from the subjects.

Yet another aspect of the invention pertains to a method for inhibiting the development or progression of Type I diabetes in a subject by administering to the subject a proinsulin peptide compound which modulates an immunological response by T cells of Type I diabetic subjects.

DETAILED DESCRIPTION OF THE INVENTION

This invention pertains to proinsulin peptide compounds which modulate an immunological response by T cells of Type I diabetic subjects and to the use of such compounds to detect and treat DM-I. (The terms Type I diabetes, insulin-dependent diabetes and DM-I are used interchangeably throughout the application.) The invention is based, at least on part, on the discovery that T cells specific for a proinsulin peptide of the invention are present in the circulation of humans with DM-I at a much greater frequency than in the circulation of non-diabetic controls. Additionally, T cell clones specific for a proinsulin peptide of the invention can cause diabetes when transferred to naive, genetically appropriate animals. These data are consistent with the proinsulin region from which the peptide is derived being a specific autoantigen attacked during the generation of DM-I. Accordingly, methods related to the diagnosis, therapy and prevention of DM-I using the proinsulin peptide compounds are provided.

I Proinsulin Peptide Compounds

One aspect of the invention pertains to proinsulin peptide compounds which modulate an immunological response from T cells of Type I diabetic subjects. The language "proinsulin peptide compound" as used herein is intended to include peptides derived from proinsulin (i.e., peptides having the amino acid sequence of a region of native proinsulin) as well as modified forms of such peptides. These modified forms include peptides having amino acid substitutions compared to the native proinsulin sequence but which retain certain structural and functional characteristics, peptides having covalent modifications (e.g., end terminal or side chain modifications), peptide analogs and mimetics and peptides derived from other proteins that are homologous to proinsulin within the region from which the peptide is derived.

The proinsulin peptide compounds of the invention are capable of modulating an immunological response from T cells of Type I diabetic subjects. The language "modulation" is intended to include either stimulation or inhibition of immunological responses. Accordingly, in various embodiments of the invention, the peptide compound can be a "stimulatory peptide compound" (i.e., a compound that stimulates an immunological response from T cells of Type I diabetic subjects) or an "inhibitory peptide compound" (i.e., a compound that inhibits an immunological response from T cells of Type I diabetic subjects). The language "inhibitory peptide compound" is intended to include peptides that inhibit T cell responses to a native proinsulin peptide (or other similar stimulatory peptide compounds).

Figure 1:
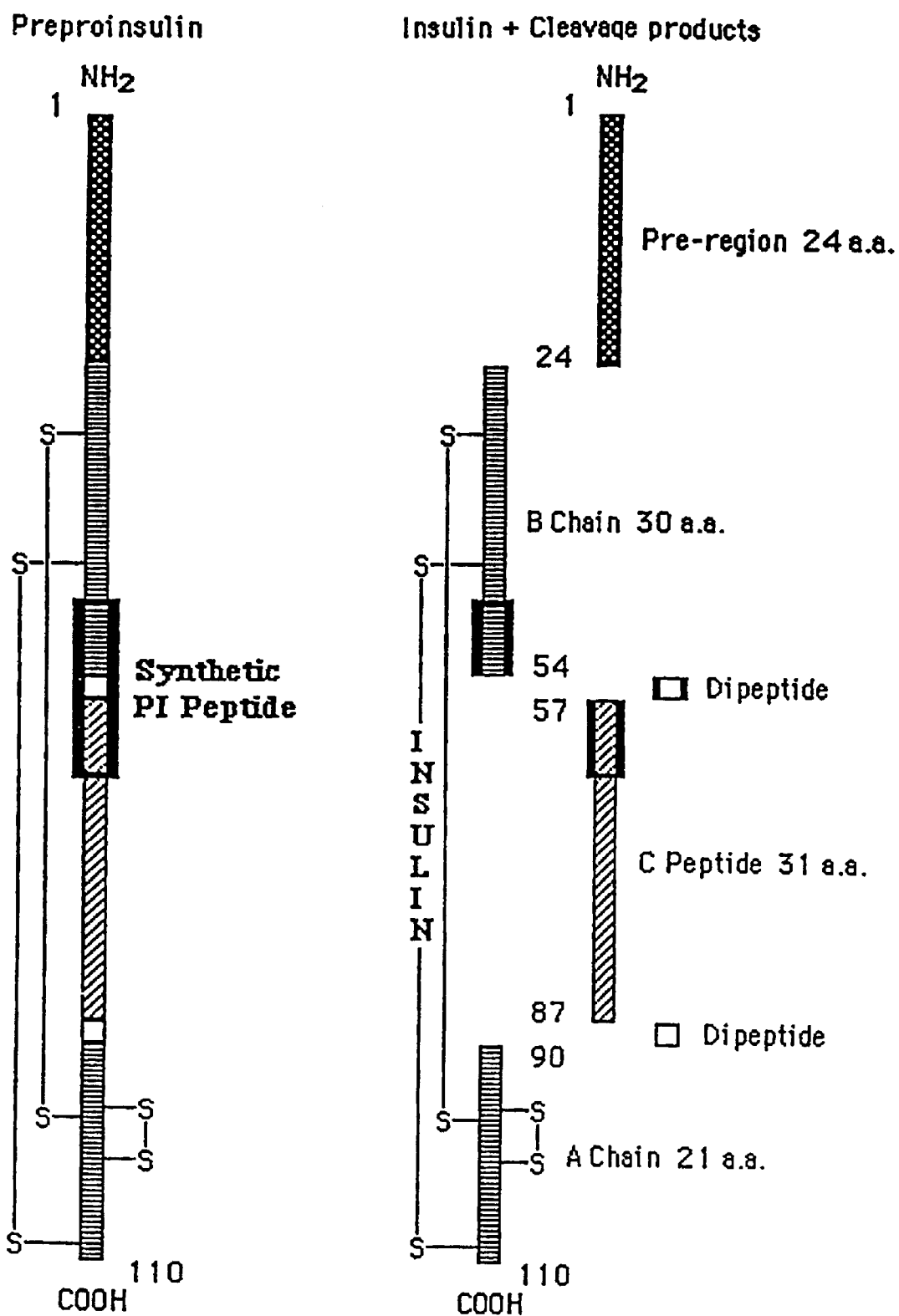
FIG. 1 is a schematic diagram of the location of synthetic peptide encompassing the MHC class II (RT1.B/D) binding motif relative to the structure of proinsulin prior to enzymatic cleavage into insulin (A+B chains linked by disulfide bonds) and C-peptide. The binding motif spans amino acids of the B and C chains in proinsulin containing one pair of basic (Arg-Arg) residues cleaved by a site-specific endoprotease during processing.

A schematic diagram of unprocessed (i.e., immature) and processed (i.e., mature) forms of insulin is shown in FIG. 1. As used herein, the language "proinsulin" refers to the immature form of insulin that includes the amino acid residues of the B chain, C peptide and A chain linked contiguously from the amino terminus to the carboxy terminus of the protein (amino acid residues 25 to 110 in FIG. 1). Upon normal processing, proinsulin is cleaved at the junction between the B chain and the C peptide, and between the C-peptide and the A chain to generate mature B chain and A chain. The language "preproinsulin" refers to the immature form of insulin that, in addition to the proinsulin sequences, includes a leader sequence linked contiguously to the amino-terminus of the B chain (amino acid residues 1–24 in FIG. 1). Upon normal processing of preproinsulin, the leader sequence is cleaved from the B chain. Since the entire coding sequence of proinsulin is contained within preproinsulin, it will be appreciated that peptides described herein as being derived from a particular region of proinsulin may also be derived from the equivalent region of preproinsulin.

Preferred proinsulin peptide compounds of the invention are derived from a region of proinsulin that spans the junction between the B chain and the C peptide of proinsulin. A peptide derived from such a region is illustrated schematically in FIG. 1 (labeled "synthetic PI peptide"). The complete nucleotide and amino acid sequences of human preproinsulin are shown in SEQ ID NOs: 1 and 2, respectively (see also Bell, G. et al. (1979) *Nature* 282:525–527; Sures, I. et al. (1980) *Science* 208:57–59). Using the amino acid sequence numbering of SEQ ID NO: 2, the B chain of human proinsulin corresponds to amino acid residues 25–54 and the C-peptide corresponds to amino acid residues 57–87 (the dipeptide of residues 55–56 is cleaved from proinsulin during processing). Accordingly, as used herein, a region of proinsulin that "spans the junction between the B chain and the C peptide of proinsulin" refers to a region encompassing amino acid residues of both the B chain and C peptide, including at least the junctional residues 30–33. A preferred region spanning this junction encompasses amino acid residues from about position 47 to about position 63.

In one embodiment of the invention, the proinsulin peptide compound that modulates an immunological response from T cells of Type I diabetic subjects is a "stimulatory proinsulin peptide compound". The language a "stimulatory proinsulin peptide compound" is intended to include peptide compounds that stimulate T cell responses, such as T cell proliferation and/or cytokine production. Preferably, the stimulatory proinsulin peptide compound is identical to a region of proinsulin that spans the junction between the B chain and the C peptide of proinsulin, as described above. A particularly preferred stimulatory peptide compound is derived from human proinsulin. In one embodiment, the peptide comprises an amino acid sequence:

$Y_1$-(Xaa)$_n$-(Ser/Thr)-Pro-Lys-(Ser/Thr)-Arg-Arg-(Glu/Asp)-(Zaa)$_m$-$Y_2$ (SEQ ID NO: 3)

wherein (Xaa) and (Zaa), which may or may not be present, represent amino acid residues, n and m are integers from 1 to 15, $Y_1$ is hydrogen or an amino-derivative group and $Y_2$ is hydrogen or a carboxy-derivative group. Preferably, the peptide is about 10–35 amino acids in length (i.e., n+m=3 to 28). More preferably, the peptide is about 10–20 amino acids in length (i.e., n+m=3 to 13). Even more preferably, the peptide is about 12–17 amino acids in length (i.e., n+m=5 to 10).

In a particularly preferred embodiment, the stimulatory peptide compound derived from human proinsulin comprises an amino acid sequence: $Y_1$-Gly-Phe-Phe-Tyr-(Ser/Thr)-Pro-Lys-(Ser/Thr)-Arg-Arg-(Glu/Asp)-Ala-Glu-(Glu/Asp)-Leu-Gln-Val-Gly-$Y_2$ (SEQ ID NO: 4), corresponding to amino acid residues 47 to 64 of human preproinsulin as shown in SEQ ID NO: 2.

In addition to peptide compounds derived from human proinsulin, stimulatory proinsulin peptide compounds from the equivalent region of proinsulin from other species are encompassed by the invention. For example, a proinsulin peptide from the equivalent region (e.g., residues 47–63) of rat proinsulin I comprises an amino acid sequence: Gly-Phe-Phe-Tyr-(Ser/Thr)-Pro-Lys-(Ser/Thr)-Arg-Arg-(Glu/Asp)-Val-Glu-(Glu/Asp)-Pro-Gln-Val (SEQ ID NO: 5). A stimulatory proinsulin peptide from the equivalent region of rat proinsulin II comprises an amino acid sequence: Gly-Phe-Phe-Tyr-(Ser/Thr)-Pro-Met-(Ser/Thr)-Arg-Arg-(Glu/Asp)-Val-Glu-(Glu/Asp)-Pro-Gln-Val (SEQ ID NO: 6). (The complete nucleotide and amino sequences of the rat preproinsulin I and II genes are disclosed in Lomedico, P. et al. (1979) *Cell* 18:545–558). The amino acid sequences of proinsulins of other species are also known in the art and can be used to design similar stimulatory proinsulin peptides identical to regions spanning the B chain and C-peptide junction of proinsulin (e.g., Perler, F. et al. (1980) *Cell* 20:555–566 disclose the sequence of the chicken preproinsulin gene; Watt V. M. et al. (1985) *J. Biol. Chem.* 260: 10926–29 disclose the sequence of the guinea pig preproinsulin gene).

Proinsulin peptide compounds of the invention can be prepared by any suitable method for peptide synthesis, including chemical synthesis and recombinant DNA technology. Preferably, the peptides are chemically synthesized. Methods for chemically synthesizing peptides are well known in the art (see e.g., Bodansky, M. *Principles of Peptide Synthesis,* Springer Verlag, Berlin (1993) and Grant, G. A (ed.). *Synthetic Peptides: A User's Guide,* W. H. Freeman and Company, New York (1992). Automated peptide synthesizers are commercially available (e.g., Advanced ChemTech Model 396; Milligen/Biosearch 9600). Methods for preparing peptides by recombinant expression in a host cell of DNA encoding the peptide are also well known in the art (see e.g., Sambrook et al. (1989) *Molecular Cloning: A Laboratory Manual,* 2nd Edition, Cold Spring Harbor Laboratory Press).

In addition to proinsulin peptide compounds having an amino acid sequence that is identical to a particular region of native proinsulin (e.g., preferably the region spanning the B chain-C peptide junction of proinsulin), the invention also encompasses proinsulin peptide compounds that are "substantially similar" to a native region of proinsulin. Peptide compounds that are substantially similar to a native region of proinsulin may be stimulatory (i.e., compounds that stimulate an immunological response by T cells of Type I diabetic subjects) or, alternatively, inhibitory (i.e., compounds that inhibit an immunological response by T cells of a Type I diabetic subjects). Peptide compounds described herein as being "substantially similar" to a particular region of proinsulin (e.g., the region spanning the B chain-C peptide junction of proinsulin) include peptides that retain certain structural and functional features of the native peptide yet differ from the native proinsulin amino acid sequence within the particular region at one or more amino acid position (i.e., by amino acid substitutions). For example, a stimulatory peptide that is substantially similar to a native proinsulin peptide retains the ability to stimulate T cell responses by T cells of Type I diabetic subjects, whereas an inhibitory peptide that is substantially similar to a native proinsulin peptide retains the ability to bind to major histocompatibility complex (MHC) molecules but lacks the ability to stimulate T cell responses by T cells of Type I diabetic subjects.

It is well accepted in the art that antigenic peptides are composed essentially of three categories of amino acid positions: 1) positions necessary for interaction of the peptide with MHC molecules (referred to herein as "MHC contact residues"), 2) positions necessary for interaction of the peptides with the T cell receptor (TCR) complex to thereby stimulate T cell activation (referred to herein as "TCR contact residues") and 3) "neutral" positions that are not critical either for MHC contact or TCR contact (see e.g., Rothbard, J. B. and Gefter, M. L. (1991) *Ann. Rev. Immunol.* 9:527–565; Jorgensen, J. L. et al. (1992) *Ann. Rev. Immunol.* 10:835–873; Rothbard, J. B. and Taylor, W. R. (1988) *EMBO J.* 7:93–100; DeLisi C. and Berzofsky, J. (1985) *Proc. Natl. Acad. Sci. USA* 82:7048; Berzofsky, J. et al. (1988) in *Immunological Reviews,* pp. 5–31, Copenhagen, Denmark: Munksgaard; Margalit, H. et al. (1987) *J. Immunol.* 138:2213–2229; O'Sullivan, D. et al. (1990) *J. Immunol.* 145:1799–1808; Corr, M et al. (1993) *J. Exp. Med.* 178:1877–1892; Falk, K. et al. (1994) *Immunogenetics* 39:230–242; Sidney, J. et al. (1994) *J. Immunol.* 152:4516–4525; Chicz, R. M. et al. (1993) *J. Exp. Med.* 178:27–47; Kropshofer, H. et al. (1992) *J. Exp. Med.* 175:1799–1803).

Accordingly, a stimulatory peptide compound substantially similar to a native stimulatory proinsulin peptide can be selected that has amino acid substitutions at one or more neutral position but retains the critical MHC contact residues and TCR contact residues such that the peptide retains both the capacity to bind MHC molecules and the capacity to stimulate T cell responses. Additionally or alternatively, the stimulatory peptide compound may have amino acid substitutions at one or more positions involved in MHC contact and/or TCR contact as long as the substitutions do not alter the ability of the peptide to stimulate T cell responses (e.g., conservative amino acid substitutions at the MHC and/or TCR contact positions may be tolerated).

In contrast to the above-described modified stimulatory peptide compounds, an inhibitory peptide compound substantially similar to a native proinsulin peptide can be selected that retains the capacity to bind to MHC molecules but lacks the capacity to stimulate an immunological response by T cells of Type I diabetic subjects. Thus, these inhibitory peptide compounds have amino acid substitutions at critical TCR contact residues such that the peptide cannot stimulate T cell responses but retains the critical MHC contact residues (or has tolerated conservative amino acid substitutions at the critical MHC contact positions) such that the peptide can still bind MHC molecules. The inhibitory peptide compounds may also have substitutions at neutral residues.

Stimulatory or inhibitory peptides altered from the native proinsulin sequence can be prepared by substituting amino acid residues within a native proinsulin peptide and selecting peptides with the desired stimulatory or inhibitory activity. For example, amino acid residues of the proinsulin peptide can be systematically substituted with other residues and the substituted peptides can then be tested in standard assays for evaluating the effects of such substitutions on immunological responses. Typically, to retain functional activity, conservative amino acid substitutions are made. As used herein, the language a "conservative amino acid substitution" is intended to include a substitution in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), P-branched side chains (e.g., threonine, valine, isoleucine) and aromatic side chains (e.g., tyrosine, phenylalanine, tryptophan, histidine). Other generally preferred substitutions involve replacement of an amino acid residue with another reside having a small side chain, such as alanine or glycine. For example, a panel of proinsulin peptide analogs of the stimulatory rat proinsulin peptide shown in SEQ ID NO: 5 is synthesized to contain alanine substitutions throughout the peptide, such as the panel of peptides shown below:

AAFYAPKSRREVEDPAA (SEQ ID NO: 7)

AAFYTAKSRREVEDPAA (SEQ ID NO: 8)

AAFYTPASRREVEDPAA (SEQ ID NO: 9)

AAFYTPKARREVEDPAA (SEQ ID NO: 10)

AAFYTPKSAREVEDPAA (SEQ ID NO: 11)

AAFYTPKSRAEVEDPAA (SEQ ID NO: 12)

AAFYTPKSRRAVEDPAA (SEQ ID NO: 13)

AAFYTPKSRREAEDPAA (SEQ ID NO: 14)

AAFYTPKSRREVADPAA (SEQ ID NO: 15)

AAFYTPKSRREVEAPAA (SEQ ID NO: 16)

Studies with other antigenic peptides have indicated that substitutions of non-critical amino acid residues with alanine residues are well tolerated (e.g., the peptide retains the ability to bind MHC molecules; see Jardetzky et al. (1990) *EMBO J.* 9:1797–1803). Amino acid substituted peptides can be prepared by standard techniques, such as automated chemical synthesis, as described further above.

The effect of the amino acid substitutions on the ability of the peptide to bind MHC molecules and/or stimulate T cell responses is tested in standard assays for evaluating immunological responses. Preferably, proinsulin-specific T cell clones or hybridomas are used in these assays. T cell clones can be prepared as described in Examples 1 and 3. T cell hybridomas can be prepared from the T cell clones by standard methods, for example by fusing a proinsulin peptide-specific T cell clone with a TcRαβ⁻ thymoma (such as the BW5147 cell line) using polyethylene glycol. Antigen specificity of the proinsulin-specific T cells is monitored by routine stimulation with proinsulin peptide and assay of antigen-specific, interleukin-2 (IL-2) production. In a standard assay for IL-2 production, culture supernatants are assayed for the presence of IL-2 in a bioassay using an IL-2 dependent cell line, such as HT-2 cells. The supernatant is added to the HT-2 cells for 24 hours, followed by an additional 12–14 hour period of incubation in the presence of $^3$H-thymidine ($^3$H-TdR), after which the cells are harvested and $^3$H-TdR uptake is measured. Other suitable assays for IL-2, such as an enzyme linked immunosorbent assay, are well known in the art.

In one assay for evaluating amino acid-substituted peptides, the ability of the substituted peptides to directly stimulate a proinsulin peptide-specific T cell clones and/or hybridomas is assessed. A proinsulin-specific T cell clone and/or hybridoma is tested for stimulation by the panel of proinsulin peptide analogs with amino acid substitutions, typically in a range of concentrations between 0.5–20 μg/ml. Stimulatory peptide compounds that retain the ability to activate the proinsulin-specific T cell clones and/or hybridoma are selected based on their ability to stimulate IL-2 production by the clone or hybridoma, as described above.

In another assay for evaluating amino acid-substituted peptides, the ability of the substituted peptides to compete with the wild-type proinsulin peptide for binding to an MHC molecule on the surface of an antigen presenting cell is assessed. Each substituted proinsulin peptide analog is preincubated with irradiated antigen presenting cells (e.g., for 2 hours) prior to the addition of wild-type proinsulin peptide and a proinsulin-specific T cell clone or hybridoma. Supernatants are harvested after an appropriate period of time (e.g., 24 hours) and assayed for the presence of IL-2, as described above. A competitive inhibitor is identified by its ability to inhibit IL-2 production by the T cell clone or hybridoma that is normally induced by the stimulatory proinsulin peptide. Moreover, an inhibitory peptide compound can be selected based upon the combined results of the direct stimulation assay and the competitive inhibition assay, for example, an inhibitory peptide compound is selected that lacks the ability to directly stimulate T cell responses but retains the ability to competitively inhibit T cell responses against the native proinsulin peptide. The ability of wild-type and substituted peptides to bind to MHC molecules also can be directly assessed using labeled peptides and purified MHC molecules in binding assays (e.g., equilibrium dialysis, column binding assays etc., for example as described in Sette, A. (1987) *Nature* 328:395–399).

Based upon animal studies (described further in Examples 1 and 2), a predicted MHC binding motif of the preferred proinsulin peptide compounds of the invention comprises an amino acid sequence: (Ser/Thr)-Xaa-Xaa-Xaa-Xaa-Xaa-(Glu/Asp) (SEQ ID NO: 17), wherein Xaa represent any amino acid. The language "MHC binding motif" refers to a pattern of amino acid residues present within a peptide (or region of a whole protein) that allow the peptide to bind to the antigenic binding site of an MHC. molecule. That is, the binding motif for a particular MHC molecule defines the critical amino acid residues of a peptide fragment that are necessary for binding of the fragment to the MHC molecule. The region of proinsulin spanning the B chain-C peptide junction (e.g., amino acid residues 47–63), from which preferred proinsulin peptides of the invention are derived, includes two of these predicted MHC binding motifs: Thr51-

Glu57 and Ser54-Asp60. The involvement of these residues in MHC binding can be directly evaluated by preparing a panel of proinsulin peptides containing amino acid substitutions (e.g., alanine substitutions) at these positions. An additional peptide composed entirely of alanines except for Thr51, Ser54, Glu57 and Asp 60 can also be tested. Thus, an example of a panel of peptides for evaluating the MHC binding motif of the proinsulin peptides is listed below:

GFFYAPKSRRAVEDPQV (SEQ ID NO: 18)
GFFYTPKARREVEAPQV (SEQ ID NO: 19)
AAAATAASAAEAADAAA (SEQ ID NO: 20)

The activity of these peptides can be assessed in the direct T cell stimulation assay and/or the competitive inhibition assay, described above, to evaluate the involvement of the (Ser/Thr)-(Glu/Asp) motif in the MHC binding ability of the peptides.

In addition to amino acid-substituted proinsulin peptides, the invention also encompasses proinsulin peptide compounds having other modifications. For example, the amino-terminus or carboxy-terminus of the peptide can be modified. The language "amino-derivative group" (e.g., $Y_1$ in the formula presented above) is intended to include amino-terminal modifications of the peptide compounds of the invention. Examples of N-terminal modifications include alkyl, cycloalkyl, aryl, arylalkyl, and acyl groups. A preferred N-terminal modification is acetylation. The N-terminal residue may be linked to a variety of moieties other than amino acids such as polyethylene glycols (such as tetraethylene glycol carboxylic acid monomethyl ether), pyroglutamic acid, succinoyl, methoxy succinoyl, benzoyl, phenylacetyl, 2-, 3-, or 4-pyridylalkanoyl, aroyl, alkanoyl (including acetyl and cycloalkanoyl e.g., cyclohexylpropanoyl), arylakanoyl, arylaminocarbonyl, alkylaminocarbonyl, cycloalkylaminocarbonyl, alkyloxycarbonyl (carbamate caps), and cycloalkoxycarbonyl, among others. The language "carboxy-derivative group" (e.g., $Y_2$ in the formula presented above) is intended to include carboxy-terminal modifications of the peptide compounds of the invention. Examples of modifications of the C-terminus include modification of the carbonyl carbon of the C-terminal residue to form a carboxyterminal amide or alcohol (i.e., as reduced form). In general, the amide nitrogen, covalently bound to the carbonyl carbon on the C-terminal residue, will have two substitution groups, each of which can be hydrogen, alkyl or an alkylaryl group (substituted or unsubstituted). Preferably the C-terminal is an amido group, such as —$CONH_2$, —$CONHCH_3$, —$CONHCH_2C_6H_5$ or —$CON(CH_3)_2$, but may also be 2-, 3-, or 4-pyridylmethyl, 2-, 3-, or 4-pyridylethyl, carboxylic acid, ethers, carbonyl esters, alkyl, arylalkyl, aryl, cyclohexylamide, piperidineamide and other mono or disubstituted amides. Other moieties that can be linked to the C-terminal residue include piperidine-4-carboxylic acid or amide and cis- or trans-4-amino-cyclohexanecarboxylic acid or amide.

Moreover, modification of one or more side chains of non-critical amino acid residues (e.g., "neutral" residues) may be tolerated without altering the function of the peptide. A covalent modification of an amino acid side chain or terminal residue may be introduced into the peptide by reacting targeted amino acid residues of the peptide with an organic derivative agent that is capable of reacting with selected side chains or terminal residues. Examples of typical side chain modifications are described further below:

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloro-mercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imodoesters such as methyl picolinimidate; pyridoxal phosphate; pyridoxal; chloroborohydride; trinitobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino groups.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3-(4-azonia-4,4-demethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton (1983) *Proteins: Structure and Molecular Properties,* W. H. Freeman & Co., San Francisco, pp. 79–86).

The activity of covalently modified peptides (e.g., end-terminal or side chain modified peptides) can be evaluated in the direct T cell stimulation assay and/or the competitive inhibition assay, described above.

The proinsulin peptide compounds of the invention also include peptide analogs and peptide mimetics of native proinsulin peptides. The language "peptide analog" or "peptide mimetic" refers to a compound composed of linked residues such that the compound mimics the structure of a native proinsulin peptide. A "residue" refers to an amino acid or amino acid mimetic incorporated in the peptide compound by an amide bond or amide bond mimetic. Approaches to designing peptide mimetics and analogs are known in the art. For example, see Farmer, P. S. in *Drug Design* (E. J. Ariens, ed.) Academic Press, New York, 1980, vol. 10, pp. 119–143; Ball. J. B. and Alewood, P. F. (1990) *J. Mol. Recognition* 3:55; Morgan, B. A. and Gainor, J. A. (1989) *Ann. Rep. Med. Chem.* 24:243–252; and Freidinger, R. M. (1989) *Trends Pharmacol. Sci.* 10:270.

An "amino acid mimetic" refers to a moiety, other than a naturally occurring amino acid, that conformationally and functionally serves as a substitute for a particular amino acid in a peptide compound without adversely interfering to a significant extent with the function of the peptide (e.g., interaction of the peptide with an MHC molecule). In some circumstances, substitution with an amino acid mimetic may actually enhance properties of the peptide (e.g., interaction of the peptide with an MHC molecule). Examples of amino acid mimetics include D-amino acids. Proinsulin peptide compounds substituted with one or more D-amino acids may be made using well known peptide synthesis procedures. The effect of amino acid substitutions with D-amino acids can be tested using assays as described above for substitutions of L-amino acids. Studies with other antigenic peptides on the effect of D-amino acid substitutions on the MHC binding ability of the peptides have shown that single D-amino acid substitutions at critical MHC contact positions typically decrease the affinity of the peptide for MHC molecules but that D-amino acid substitutions made outside of these positions are relatively well tolerated. See e.g., PCT Publication No. WO 92/02543 by Gaeta et al.

The peptide analogs or mimetics of the invention include isosteres. The term "isostere" as used herein refers to a sequence of two or more residues that can be substituted for a second sequence because the steric conformation of the first sequence fits a binding site specific for the second sequence. The term specifically includes peptide back-bone modifications (i.e., amide bond mimetics) well known to those skilled in the art. Such modifications include modifications of the amide nitrogen, the α-carbon, amide carbonyl, complete replacement of the amide bond, extensions, deletions or backbone crosslinks. Several peptide backbone modifications are known, including $\psi[CH_2S]$, $\psi[CH_2NH]$, $\psi[CSNH_2]$, $\psi[NHCO]$, $\psi[COCH_2]$, and $\psi[(E)$ or $(Z)$ $CH=CH]$. In the nomenclature used above, $\psi$ indicates the absence of an amide bond. The structure that replaces the amide group is specified within the brackets. Other examples of isosteres include peptides substituted with one or more benzodiazepine molecules (see e.g., James, G. L. et al. (1993) *Science* 260:1937–1942).

Other possible modifications include an N-alkyl (or aryl) substitution ($\psi[CONR]$), backbone crosslinking to construct lactams and other cyclic structures, or retro-inverso amino acid incorporation ($\psi[NHCO]$). By "inverso" is meant replacing L-amino acids of a sequence with D-amino acids, and by "retro-inverso" or "enantio-retro" is meant reversing the sequence of the amino acids ("retro") and replacing the L-amino acids with D-amino acids. For example, if the parent peptide is Thr-Ala-Tyr, the retro modified form is Tyr-Ala-Thr, the inverso form is thr-ala-tyr, and the retro-inverso form is tyr-ala-thr (lower case letters refer to D-amino acids). Compared to the parent peptide, a retro-inverso peptide has a reversed backbone while retaining substantially the original spatial conformation o the side chains, resulting in a retro-inverso isomer with a topology that closely resembles the parent peptide and is able to bind the selected MHC molecule. See Goodman et al. "*Perspectives in Peptide Chemistry*" pp. 283–294 (1981). See also U.S. Pat. No. 4,522,752 by Sisto for further description of "retro-inverso" peptides.

The modified forms of proinsulin peptides of the invention, including L- or D-amino acid substitutions, covalent modification of end termini or side chains, and peptide analogs and mimetics can be selected for desired alterations of the physical or chemical properties of the peptide, for example, increased stability, solubility, bioavailability, increased or decreased immunogenicity, etc.

Although the preferred peptide compounds of the invention are derived from a region of proinsulin, or are modified forms of a peptide derived from proinsulin, it will be appreciated by those skilled in the art that peptides derived from other proteins that are homologous to proinsulin within the region from which the peptide is derived may also be useful for modulating immunological responses by T cells of Type I diabetic subjects. For example, peptide compounds of the invention may be derived from proteins having a region that is homologous to the region of proinsulin spanning the B chain-C peptide junction (e.g., amino acids 47–63 of proinsulin). One hypothesis to explain the initiating pathological event leading to an autoimmune response against an autoantigen is that the autoantigen mimics an environmental or microbial antigen to which the subject has been exposed. Thus, this environmental or microbial antigen serves as the immunizing stimulus that activates the autodestructive immune elements. Accordingly, the amino acid sequence of the region of proinsulin spanning the B chain-C peptide junction (e.g., amino acids 47–63 of proinsulin) can be compared to that of other proteins (e.g., potential environmental or microbial antigens) to identify proteins with a homologous region. Peptides derived from such a homologous region of another protein, or modified peptides thereof, modified as described herein, may also be useful for modulating (e.g., stimulating or inhibiting) immunological responses by T cells of Type I diabetic subjects.

II. Pharmaceutical Compositions

The proinsulin peptide compounds of the invention can be formulated into compositions suitable for pharmaceutical administration. The pharmaceutical composition typically includes a proinsulin peptide (or modified form thereof as described above) and a pharmaceutically acceptable carrier. In a preferred embodiment, the pharmaceutical composition includes a proinsulin peptide compound identical or substantially similar to a region of proinsulin that spans the junction between the B chain and the C peptide of proinsulin. Preferably, the proinsulin peptide is derived from human proinsulin.

As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (i.e., proinsulin peptide or derivative thereof) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of invariant chain protein or peptide is then introduced into the container. The container is then swirled by hand to free lipid material from the sides of the container and to disperse lipid aggregates, thereby forming the liposomal suspension.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals.

In one embodiment, the pharmaceutical composition comprises a tolerogenic amount of a proinsulin peptide compound of the invention. As used herein, the language a "tolerogenic amount" is intended to include an amount of peptide compound sufficient to induce unresponsiveness to the peptide compound, or a related peptide or a protein from which the peptide is derived (e.g., proinsulin), in a subject. While not intending to be limited by mechanism, unresponsiveness to the compound may result from induction of anergy in T cells specific for the compound, deletion (e.g., destruction) of T cells specific for the antigen or induction of T suppressor cell circuits. The tolerogenic amount of a compound necessary to induce unresponsiveness in a subject is likely to vary depending upon the particular form of peptide compound used, the route of administration, the state of disease in the subject, etc. Animal models accepted in the art as models of human Type I diabetes (e.g., the Biobreeding rat or the NOD mouse) can be used to test particular peptide compounds, routes of administration etc., to determine appropriate tolerogenic amounts of the peptide compounds of the invention.

III. Methods for Detecting an Indicator of DM-I in a Subject

The proinsulin peptide compounds of the invention can be used in assays to detect an indicator of Type I diabetes in a subject. As described in further detail in Example 3, biological samples from human Type I diabetic patients exhibit increased immunological activity directed against a proinsulin peptide of the invention than do biological samples from non-diabetic control humans. Accordingly, immunological activity directed against a stimulatory proinsulin peptide compound of the invention can be detected as an indicator of Type I diabetes in a subject.

The invention provides a method for detecting an indicator of Type I diabetes in a subject, comprising a) obtaining a biological sample from the subject;

b) contacting the sample with a proinsulin peptide compound that stimulates an immunological response by T cells of Type I diabetic subjects; and c) detecting an immunological activity in the sample against the proinsulin peptide compound as an indicator of Type I diabetes in the subject.

Proinsulin peptide compounds suitable for use in the method include the stimulatory compounds described in detail hereinbefore. Preferably, the proinsulin peptide compound is identical or substantially similar to a region of proinsulin that spans the junction between the B chain and the C peptide of proinsulin, as described above. For detection of an indicator of DM-I in biological samples from humans, the proinsulin peptide compound preferably is derived from human proinsulin.

Typically, the biological sample used in the method is a blood sample from the subject, or a subfraction thereof, such as nucleated cells (e.g., lymphocytes) or serum, although any suitable biological sample that may contain an immunological activity can be used. Blood samples, or other biological samples, can be obtained from a subject by standard techniques. Furthermore, blood samples can be fractionated (e.g., to obtain nucleated cells, serum, etc.) by standard techniques.

In one embodiment of the method, the immunological activity that is detected is a T cell response to the proinsulin peptide compound. For example, peripheral blood mononuclear cells, or purified T cells, from a blood sample from the subject can be cultured in the presence of the compound. After a sufficient period of time in which to elicit a T cell response to the compound, the responsiveness of the T cells to the compound is determined. T cell responsiveness can be assessed, for example, by measuring T cell proliferation (e.g., by standard tritiated thymidine uptake) or production of cytokines (described further below).

Prior to or alternative to measuring T cell responsiveness, proinsulin-specific T cell clones can be prepared from the biological sample and quantitated (e.g., see Example 3). The frequency of proinsulin-specific T cells in the biological sample can be determined by limiting dilution analysis (e.g., as described in Sabbaj, S et al. (1992) *J. Clin. Immunol.* 12:216–224). Alternatively, the frequency of proinsulin specific T cells can be determined using the hypoxanthine guanine phosphoribosyltransferase (hprt) clonal assay (as described in Allegretta, M. et al. (1990) *Science* 247:719–721; and Lodge, P. et al. (1994) *Neurology* 44(Suppl. 2):A147). A key feature of this clonal assay technique is that T cells detected by this system are presumed to have undergone multiple cycles of in vivo stimulation in response to the antigen of interest prior to cloning. Thus, it is considered to reflect an accurate picture of T cell specificity and clonal activity in the subject by utilizing a test that can be performed in vitro. The results can be compared to non-diabetic controls.

Alternative or in addition to measuring T cell proliferation, T cell cytokine production can be measured as an indicator of immunological activity against the proinsulin peptide compound. T cell cytokine production can be assayed, for example, by a standard enzyme linked inmmunosorbent assay (ELISA) or radioimmunoassay (RIA) specific for the particular cytokine (e.g., proinflammatory cytokines such as interleukin-2 [IL-2], interferon-γ [IFN-γ] and tumor necrosis factor/lymphotoxin [TNF/LT]). In a nonlimiting example of the method, bulk cultures ($5 \times 10^6$ cells) of peripheral blood mononuclear cells from the subject are initiated in an appropriate medium containing the proinsulin peptide. Seven days after the initiation of the bulk cultures, IL-2 (as a T cell growth factor) is added and then renewed every 3 to 4 days. At 14 days post initiation of the culture, cells are harvested and adjusted to $2 \times 10^6$ cells/ml in fresh medium lacking IL-2 for 48 hours. After 48 hours, supernatants are harvested to be assayed for the presence of cytokines. The cultures can be maintained, for example, up to 4 weeks, with the supernatants periodically monitored for cytokine production. The supernatants can be frozen until assayed. Kits for assaying cytokine levels are commercially available (e.g., an ELISA for IL-2 is available from Genzyme; an ELISA for TNF/LT is available from R & D Systems; an RIA for IFN-γ is available from Centocor). Again, the results can be compared to non-diabetic controls.

In another embodiment of the method of detecting an indicator of Type I diabetes in a subject, the immunological activity that is detected by the method is antibody binding to the preproinsulin peptide compound. A biological sample containing immunoglobulin (e.g., serum) can be obtained from the subject and contacted with the proinsulin peptide compound to determine whether antibodies specific for the proinsulin peptide are present in the sample. Standard methods can be used to detect the presence of antibodies specific for the proinsulin peptide compound, such as ELISAs and RIAs.

IV. Methods for Inhibiting the Development or Progression of DM-I in a Subject

Another aspect of the invention pertains to methods for inhibiting the development or progression of Type I diabetes in a subject comprising administering to the subject a proinsulin peptide compound of the invention which modulates an immunological response by T cells of Type I diabetic subjects. The subject may suffer from Type I diabetes, may be in a "pre-diabetic" phase of the disease or may be susceptible to development of the disease (e.g., the subject may have a genetic predisposition to Type I diabetes). While not intending to be limited by mechanism, the development or progression of DM-I in subjects can be inhibited using peptide compounds as described herein by, for example, depleting pathogenic T cells, inducing anergy in pathogenic T cells or stimulating specific suppressor circuits to inhibit the progression of islet cell destruction.

In one embodiment, a stimulatory proinsulin peptide compound of the invention, as described in detail above, is administered to a subject to inhibit the development or progression of Type I diabetes. Studies in other autoimmune systems have demonstrated that peptides that stimulate antigen-specific T cell response in vitro can be used to induce T cell tolerance in vivo. For example, in experimental autoimmune encephalitis (EAE), a modified peptide of myelin basis protein that retains the ability to bind to MHC molecules has an increased ability to stimulate T cells in vitro can prevent EAE induction when administered before or after the onset of the disease (see e.g., Wraith, D. C. et al. (1989) *Cell* 59:247–255; Smilek, D. et al. (1991) *Proc. Natl. Acad. Sci. USA* 88:9633–9637). Moreover, peripheral T cell tolerance to the major cat allergen Fel d I can be induced by subcutaneous of Fel d I peptides expressing immunodominant T cell epitopes (see e.g., Briner, T. J. et al. (1993) *Proc. Natl. Acad. Sci. USA* 90:7608–7612). Accordingly, a stimulatory proinsulin peptide of the invention can be used to modulate responsiveness the responsiveness of T cells in Type I diabetic subjects by administering a tolerogenic amount of the peptide and/or by I administering the peptide by a tolerogenic route of administration. Preferred tolerogenic routes of administration are subcutaneous injection (see e.g., Briner et al., supra), oral administration (see e.g., Whitacre, C. et al. (1991) *J. Immunol.* 147:2155–2163) and intrathymic injection (see e.g., Posselt, A. M. et al. (1992) *Science* 256:1321–1324).

Additionally, a stimulatory peptide compounds of the invention, such as a modified proinsulin peptide or a modified peptide derived from an environmental or microbial antigen homologous to proinsulin may be useful for vaccinating individuals who are susceptible or predisposed to development of DM-I. Suitable peptide compounds, in an appropriate vehicle, can be administered to a susceptible individual to deplete autoaggressive immunological elements and/or to produce a protective immune response the modified peptide compound which does not crossreact with self tissue.

In another embodiment, an inhibitory peptide compound of the invention as described in detail above, is administered to a subject to inhibit the development or progression of Type I diabetes. Studies in other autoimmune systems have demonstrated that inhibitory peptides, such as MHC blocking peptides (i.e., peptides that retain the ability to bind MHC molecules but which do not stimulate T cell responses) can be used to prevent and/or treat autoimmune responses. Successful examples of this approach include the treatment of EAE (see e.g., Wauben, M. H. et al. (1992) *J. Exp. Med.* 176:667–677; Sakai, K. et al. (1989) *Proc. Natl. Acad. Sci. USA* 86:9470–9474), adjuvant arthritis (Wauben et al., supra) and diabetes in the NOD mouse (see e.g., Hurtenbach, U. et al. (1993) *J. Exp. Med.* 177:1499–1504).

A peptide compound of the invention is administered to a subject in a biologically compatible form suitable for pharmaceutical administration in vivo, by which is meant that the form of the compound is one in which any toxic effects are outweighed by the therapeutic effects of the agent. The term "subject" is intended to include living organisms which are susceptible to Type I diabetes, e.g., mammals and in particular, humans. Administration of a compound as described herein can be in any pharmacological form including a therapeutically active amount, alone or in combination with another therapeutic compound, and a pharmaceutically acceptable carrier.

Administration of a therapeutically effective amount of a compound of the invention is defined as an amount, at dosages and for periods of time, sufficient to achieve the desired result. For example, the desired result can include inhibition of at least one symptom of the DM-I, slowing or halting the progression of the disease or other clinically desirable result. A therapeutically effective amount of the compound may vary according to factors such as the disease state, age, sex, and weight of the individual, and the ability of the compound to elicit a desired response in the individual. Dosage regimens may be adjusted to provide the optimum therapeutic response. For example, the composition may be administered at once, or several divided doses may be administered daily for a period of time. The dose may be proportionally reduced as indicated by the exigencies of the therapeutic situation. The concentration of active compound in the composition will depend on absorption, inactivation, and excretion rates of the compound as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The compound can be administered for prophylactic and/or therapeutic treatments. In therapeutic applications, the compound is administered to a subject already suffering from the disease in an amount sufficient to alleviate or at least partially arrest the symptoms of the disease and/or its complications. An amount adequate to accomplish this is referred to as a "therapeutically effective dose". Amounts effective for this use may vary widely, but nonlimiting examples of therapeutic systemic dosages for the compounds described herein are those ranging from 0.1 mg to about 2,000 mg of peptide per day for a 70 kg subject, with dosages of from about 0.5 mg to about 700 mg of peptide per day being more typical. In prophylactic applications, the compound is administered to a subject susceptible or otherwise at risk for the disease in an amount sufficient to enhance the subject's own immunoregulatory capabilities. Such an amount is referred to herein as a "prophylactically effective dose". Again, amounts effective for this use may vary widely, but nonlimiting examples of prophylactic systemic dosages for the compounds described herein are those ranging from 0.1 mg to about 500 mg of peptide per day for a 70 kg subject, with dosages of from about 0.5 mg to about 200 mg of peptide per day being more typical.

The compound may be administered in a convenient manner suitable to achieve the desired result. For example, in one embodiment, the agent is administered intravenously. In another embodiment, the agent is administered orally. In yet other embodiments, the agent is administered subcutaneously, intrathymically, intramuscularly or intraperitoneally. Depending on the route of administration, the agent may be coated in a material to protect the agent from the action of enzymes, acids and other natural conditions which may inactivate the compound and/or to deliver the compound in a slow-release formulation.

The effectiveness of particular peptide compounds, dosages, carriers, routes of administration and the like can be evaluated in well characterized animal models of human Type I diabetes, wherein positive results in these animal models are predictive of efficacy in humans. Preferred animal models include the Biobreeding rat (see e.g., Parfrey, N. A. et al. (1989) *Crit. Rev. Immunol.* 9:45–65; Logothetopoulous, L. et al. (1984) *Diabetes* 33:33–36) and the NOD mouse (see e.g., Kikutani, H. et al., in *Adv. Immunol.* (F. J. Dixon, ed.), pp. 285–323, New York, N.Y.:Academic Press, (1992).

This invention is further illustrated by the following examples which should not be construed as limiting. The contents of all references, patents and published patent applications cited throughout this application are hereby incorporated by reference.

EXAMPLE 1

Proinsulin Peptide-Specific T Cell Clones Induce Insulitis

Type I diabetes (also referred to as insulin-dependent diabetes mellitus), an autoimmune disease which occurs in humans and animals, is characterized by the destruction of insulin-secreting islet β-cells of the pancreas. Epidemiological studies in man have documented a strong genetic predisposition linked to HLA-DR3, -DR4 and -DQ3.2 class II alleles of the human MHC (see e.g., Wolf, E. et al. (1983)

*Diabetologia* 24:224–230; Platz, P. et al. (1981) *Diabetologia* 21:108–115; Warram, J. et al. (1994) in *Joslin's Diabetes Mellitus,* R. Kahn and G. Weir (eds.), Philadelphia, Pa., Lea & Febiger, pp. 201–215; and Tait, B. D. et al. (1991) *Bailliere's Clin. Endocrinol. & Metab.* 5:211–228). This suggests a significant association between pathogenic pancreatic autoantigen(s) and antigen presentation to T lymphocytes in the context of these specific MHC class II molecules.

In this example, a rat MHC class II (RT1.B$^1$) binding motif was used to predict potentially autoreactive CD4$^+$ T cell epitopes in two islet β-cell constituents: the enzyme glutamic acid decarboxylase (GAD) and the insulin precursor hormone, proinsulin (PI). Seventeen-amino acid long peptide fragments of GAD and PI containing the binding motif were synthesized and used to generate peptide-specific, MHC Class II-restricted, CD4$^+$ T cell lines from DA(RP) rats (MHC type RT.1A$^a$B/D$^1$E/C$^a$). Once established, the DA(RP)-derived T cell lines specific for rat islet GAD and PI were adoptively transferred to naive DA(RP) rats. At 10 days post-transfer, insulitis had developed in rats receiving proinsulin-specific T cells, while no insulitis was observed in pancreases of rats receiving GAD-specific T cells. The pathogenic PI peptide-specific T cells are CD4$^+$/CD8$^-$ and secrete TH$_1$-like cytokines in response to antigen. Thus, this example provides a novel, antigen-specific model of autoimmune insulitis by T cells specific for a peptide fragment of proinsulin.

The following methodologies were used in this example:

Materials and Methods

Animals. DA(RP) rats, with the MHC type RT1.A$^a$B$^1$D$^1$E/C$^a$, were used in these studies. This rat strain develops neither spontaneous insulitis nor diabetes. DA(RP) strain rats were originally obtained from Dr. Heinz Kunz (Department of Pathology, University of Pittsburgh, Pittsburgh, Pa.), and a breeding colony was maintained in the Animal Research Facility of the Dartmouth Medical School, Lebanon, N.H. Both male and female DA(RP) rats were used in experiments between the ages of 50–70 days. All procedures and animal care were in accordance with the National Institutes of Health guidelines on laboratory animal welfare.

MHC Class II Binding Motif Peptide Synthesis. Sequences of the PI and GAD peptides containing the binding motif were synthesized by standard F-moc chemistry using the RapidAmide Multiple Peptide Synthesis (RaMPS) system (NEN-Dupont, Wilmington, Del.). Given that MHC Class II-restricted T cells typically recognize peptides between 13–25 amino acids in length (Zamvil, S. et al. (1986) *Nature* 324:258–260; Wraith, D. C. et al. (1989) *Cell* 59:247–255), GAD and PI peptides were extended by four to six amino acids on each end of the motif, and synthesized to yield 17-amino acid long peptides (designated GAD$_{412}$, GAD$_{520}$, and PI). Moreover, peptides were N-terminally acetylated to encourage α-helix formation and MHC interaction (Mains, R. et al. (1983) *Trends Neurosci.* 6:229–235).

Generation of Peptide-specific T Cell Lines and Adoptive Transfer. Individual T cell lines were generated against GAD$_{412}$, GAD$_{520}$ and PI peptides. To initiate T cell lines, peptides were emulsified in complete Freund's adjuvant (CFA) supplemented with 5 mg/ml H37RA (DIFCO, Detroit, Mich.) and injected intradermally in the hind footpads of DA(RP) rats in a final concentration of 200 μg peptide. After nine days, rats were sacrificed via Fluothane anesthesia (Ayerst Laboratories, New York, N.Y.) to obtain popliteal lymph nodes. Lymph nodes were mechanically dissociated with forceps into a single cell suspension, washed two times in phosphate buffered saline (PBS), and resuspended in initiation medium with 50 μg/ml peptide. Initiation/proliferation medium consisted of RPMI 1640, 1% autologous rat serum, 5% NCTC-109 (BioWhittaker Products, Walkersville, Md.), 2 mM glutamine, 100 U/ml penicillin, 100 μg/ml streptomycin, 100 μg/ml fingizone (ICN Biomedicals, Costa Mesa, Calif.), and 5×10$^{-5}$ M 2-mercaptoethanol (Sigma, St. Louis, Mo.). After three days, T-lymphoblasts were collected by density centrifugation using Histopaque-1.077 (Sigma), washed two times in PBS, and resuspended in medium containing 10% fetal calf serum and 5% IL-2-rich supernate from concanavalin A-stimulated spleen cells. Peptide-specific T cell lines were allowed to come to a resting state 7–10 days after the initial in vitro stimulation with peptide, then restimulated with irradiated thymocytes (2000 rad) and 20 μg/ml peptide.

For adoptive transfer studies, anti-GAD and anti-PI T cells were stimulated with either peptide (20 μg/ml) or the mitogenic lectin concanavalin-A (5 μg/ml) for 72 hr prior to intravenous (i.v.) injection into naive recipients. Ten days following i.v. transfer of peptide-specific T cells (ranging in concentrations from 25–120×10$^6$), rats were sacrificed under ether anesthesia to obtain the pancreas. Tissue was fixed in 10% formalin, embedded in paraffin, sectioned (6 microns), mounted and stained with hematoxylin and eosin.

Antigen Specificity and MHC Restriction of Peptide-specific T Cell Lines. Peptide-specific T cells were collected and co-cultured in triplicate (5–7×10$^4$/well) with or without peptide (5–20 μg/ml), irradiated (2000 rad) thymocytes (5×10$^5$/well) as antigen presenting cells (APC), OX-3, OX-6 or OX-17 (anti-RT1.B and D) antibodies, or W3/25 (anti-CD4), OX-8 (anti-CD8) antibodies for 72 hr, including a final 18 hr pulse with $^3$H-Thymidine (0.5 μCi/well). $^3$H-Thymidine incorporation was measured by liquid scintillation counting (Wallac, Gaithersburg, Md.) and the results expressed as stimulation indices±one standard deviation (SD) for triplicate cultures.

Cytokine Production Profile of Peptide-specific T cells. Proinsulin-specific T cells were tested for cytokine production in response to PI peptide. Proinsulin peptide specific levels of interleukin 2 (IL-2) and interleukin 4 (IL-4) were measured in a bioassay using IL-2-dependent HT-2 cells, and IFN-γ production was measured with an ELISA specific for rat IFN-γ (GIBCO BRL, Gaithersburg, Md.). Briefly, 100 μl aliquots of supernatant were collected from in vitro cultures of PI-specific T cells, PI peptide, APC+anti-MHC Class II antibodies at 40 hr for IL-2 and IL-4 assay, and 72 hr for IFN-γ. Interleukin-2 containing supernates were cultured with 1×10$^3$ HT-2 cells for 48 hr, including a pulse with $^3$H-Thymidine for the final 12 hr of culture. Interleukin-4 containing supernates were cultured with 1×10$^3$ HT-2 cells which had been preincubated with an IL-2 receptor antibody (PC 61.5.3, ATCC, Rockville, Md.). After 48 hr, HT-2 cells were harvested and $^3$H-Thymidine uptake measured by liquid scintillation counting.

Flow Cytometric Analyses of Peptide-specific T Cell Lines. PI-specific and GAD-specific T cells were stimulated with 20 μg/ml peptide or 5 μg/ml concanavalin A for 72 hr prior to determinations of surface antigen expression. Samples of 1×10$^6$ anti-PI T cells each were stained with primary antibody (OX-19 (CD5); W3/25 (CD4); OX-8 (CD8); R7.3 (αβ T cell receptor); OX-3, OX-6, OX-17 (RT1.B and RT1.D); OX-22 (CD45RC); 12.5–20 μg/ml protein from ascites; Harlan Bioproducts for Science, Indianapolis, Ind.) for 30 min on ice, washed twice, then incubated with fluorescein isothiocyanate (FITC)-conjugated goat anti-mouse F(ab')$_2$ antibody (Cappel-Orginon Teknika, West Chester, Pa.) for 30 minutes on ice, washed twice and fixed with 1% paraformaldehyde/PBS. Control staining consisted of cells stained with an IgG1 isotype control antibody (MOPC 21, Sigma, St. Louis, Mo.) in place of primary antibody, in addition to unstained cells and cells stained with secondary antibody only. Cells were analyzed on a FacScan flow cytometer (Becton-Dickinson, Lincoln Park, N.J.).

RINm5F Insulinoma Cells. RINm5F insulinoma cells (Gadzar, A. et al. (1980) *Proc. Natl. Acad. Sci. USA* 77:3519–3523) were obtained from Dr. Walter Hsu, Iowa State University. RIN cells were cultured in RPMI 1640 medium supplemented with 10% heat-inactivated fetal calf serum (Hyclone), 100 μg/ml streptomycin, 100 U/ml penicillin, and 2 mM L-glutamine (Bio Whittaker). Exhausted RIN cell supernatant was collected after 5 days of growth, 50–70% confluency of RIN cells. Supernates were centrifuged, sterile filtered and stored at −20° C. until use in PI-specific T cell assays. RIN cell supernate-was added in a 20% v/v concentration to PI-specific T cells in vitro.

Results

Proinsulin (PI) and GAD peptides containing the MHC Class II binding motif were synthesized and used to generate T cell lines. Table I lists the amino acid sequences of the synthetic PI and GAD peptides. FIG. 1 represents a diagram of the proximal relationship between the amino acid sequence of rat preproinsulin, the MHC Class II binding motif, and the cleavage products of insulin and C-peptide.

ment ranged from no involvement to early pen-insular inflammation, to marked insulitis. Immunohistochemical analysis revealed that PI-induced insulitis consisted primarily of CD4$^+$ T cells and macrophages, an infiltrate typical of delayed type hypersensitivity and autoimmune reactions in the rat.

Figure 2:
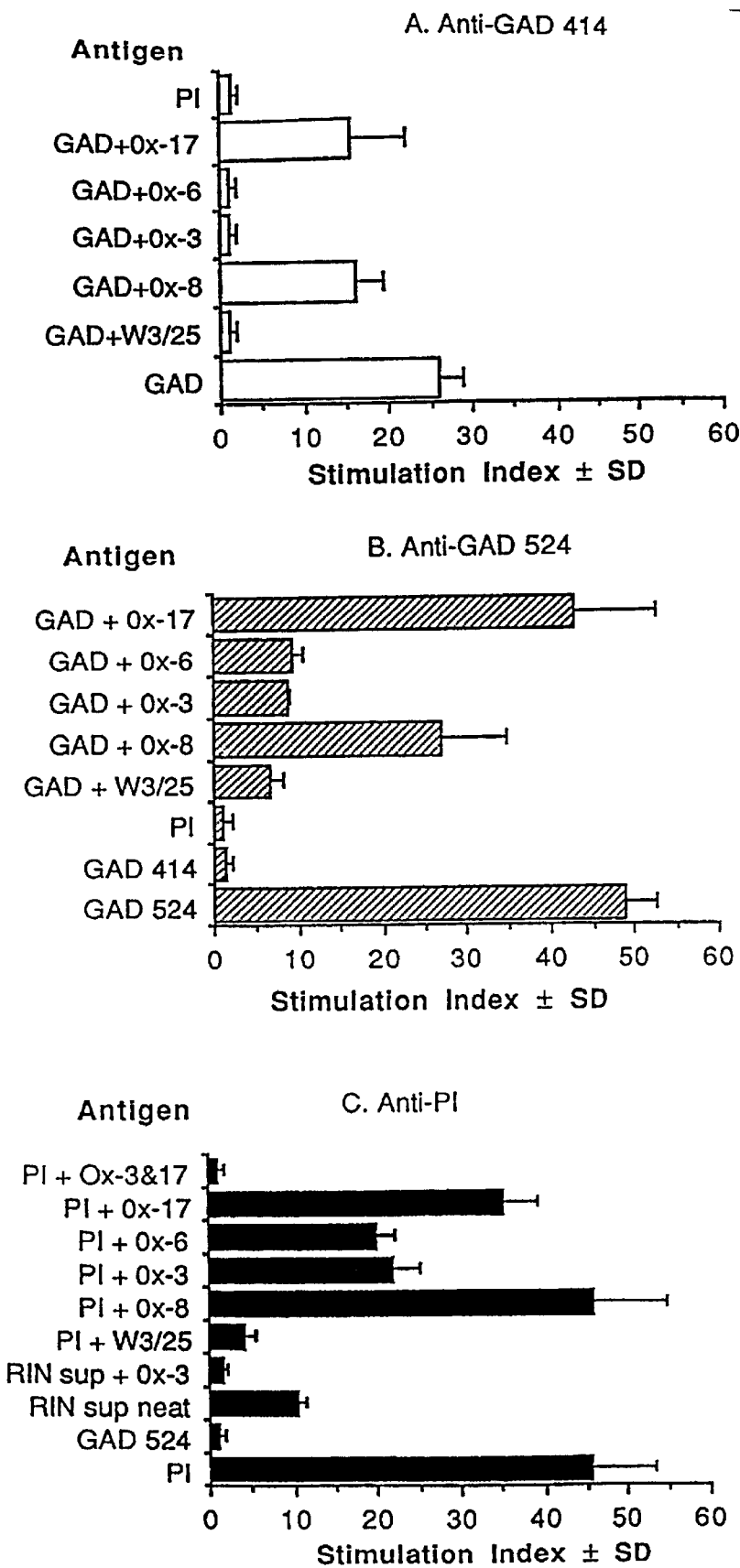
FIGS. 2A–C are graphic representations of the proliferation of T cell lines specific for $GAD_{412}$ (panel A), $GAD_{520}$ (panel B) and PI (panel C) peptides in the presence or absence of anti-MHC class II antibody (for reference, mean cpm for $GAD_{412}$ T cells incubated with APCs and medium= 850±297; $GAD_{520}$=74±30; and PI=1763±181).

The phenotypic and functional characteristics of the GAD and PI-specific T cell lines were investigated to determine antigen specificity and MHC restriction. FIG. 2 shows $^3$H-Thymidine incorporation assay results for anti-GAD and anti-PI T cell lines and their MHC Class II restriction patterns. The stimulation index (S.I.) is defined as the mean cpm of the experimental sample divided by the mean cpm of control wells (medium only). $^3$H-thymidine incorporation assays were replicated 2–3 times for cells of each line at the time of the second in vitro stimulation with peptide. GAD and PI-specific T cells responded to their respective peptides and did not crossreact with other peptides containing the class II binding motif. Proliferation of both GAD T cell lines containing the S-E binding motif was inhibited by the addition of anti-RT1.B antibody (Ox-3 & Ox-6), but not anti-RT1.D (Ox-17) antibody (FIG. 2, panel A: GAD$_{412}$; panel B: GAD$_{520}$). Proliferation of PI-specific T cells to 20 μg/ml PI peptide could be partially inhibited by antibodies against RT1.B (54–67%) and RT1.D (22–25%) molecules individually, and significantly inhibited by the addition of RT1.B and D antibodies together (>90%) (FIG. 2, panel C). This inhibitory effect of anti-MHC Class II antibodies followed the same pattern irrespective of the antigen presenting cell (APC) source used (i.e., DA(RP) or the RT1.B/D$^1$ congenic Lewis strain rat). In addition, PI-specific T cells proliferated in response to a insulin/proinsulin-containing supernatant from the rat insulinoma cell line, RINm5F, and

TABLE I

Amino Acid Sequences of Synthetic Peptides containing the MHC Class II (RT1.B$^1$) Binding Motif a) rat PROINSULIN

| | | |
|---|---|---|
| | * * | |
| PROINSULIN I | $_{47}$G F F Y T P K S R R E V E D P Q V$_{63}$ | (SEQ ID NO:5) |
| PROINSULIN II | $_{47}$G F F Y T P M S R R E V E D P Q V$_{63}$ | (SEQ ID NO:6) | b) rat islet GAD$_{412}$  $_{412}$L L Q C S A I L V K E K G I L Q G$_{428}$  (SEQ ID NO:21)

c) rat islet GAD$_{520}$  $_{520}$Y I P Q S L R G V P D S P E R R E$_{536}$  (SEQ ID NO:22)

*represents cleavage site during processing of proinsulin to insulin; Arg-Arg residues are released as a dipeptide at the separation of the insulin B-chain and C-peptide.

Proinsulin-specific and GAD-specific T cell lines were adoptively transferred to DA(RP) rats by i.v. tail vein injection. Ten days following transfer of peptide-specific T cells, pancreases were obtained and examined for signs of histopathology by staining with hematoxylin and eosin. No detectable insulitis was observed in pancreases of rats receiving GAD$_{412}$- or GAD$_{520}$-specific T cells (range= 3.0–12.0×10$^7$ cells/rat) relative to untreated pancreas. In contrast, the intravenous injection of 3.0–7.0×10$^7$ T cells/rat specific for PI peptide caused insulitis in all DA(RP) rats (n=18). The average inflammatory involvement of islets per pancreas section/per rat was 40+6% (range 21–62% per pancreas section) by day 10 post-transfer of PI-specific T cells. Within pancreas sections, the severity of islet involvethis proliferation could be blocked by the addition of anti-RT1.B antibody. Both GAD-specific and PI-specific cell proliferation was abrogated by monoclonal antibodies against CD4, but not CD8, indicating that only CD4 positive T cells responded to GAD and PI peptides.

PI-specific T cells were monitored in vitro for cytokine production in response to PI peptide with or without MHC Class II blocking antibody. PI-specific T cells secreted marked amounts of both IL-2 and IL-4 in response to PI peptide, even in the presence of antibodies to MHC Class II that inhibited proliferation. Furthermore, PI-specific T cells secreted IFN-γ in response to PI peptide alone (22.5+0.2 ng/ml) as measured by an ELISA specific for rat IFN-γ (GIBCO). IFN-γ production in response to PI peptide in combination with individual class II antibodies (Ox-3 and Ox-17) averaged 23.8+0.3 ng/ml, and then dropped to 12.5+0.2 ng/ml in cultures where $^3$H-Thymidine incorporation in response to PI peptide was significantly inhibited by the addition of Ox-3 and Ox-17 together (FIG. 2, C).

Figure 3:
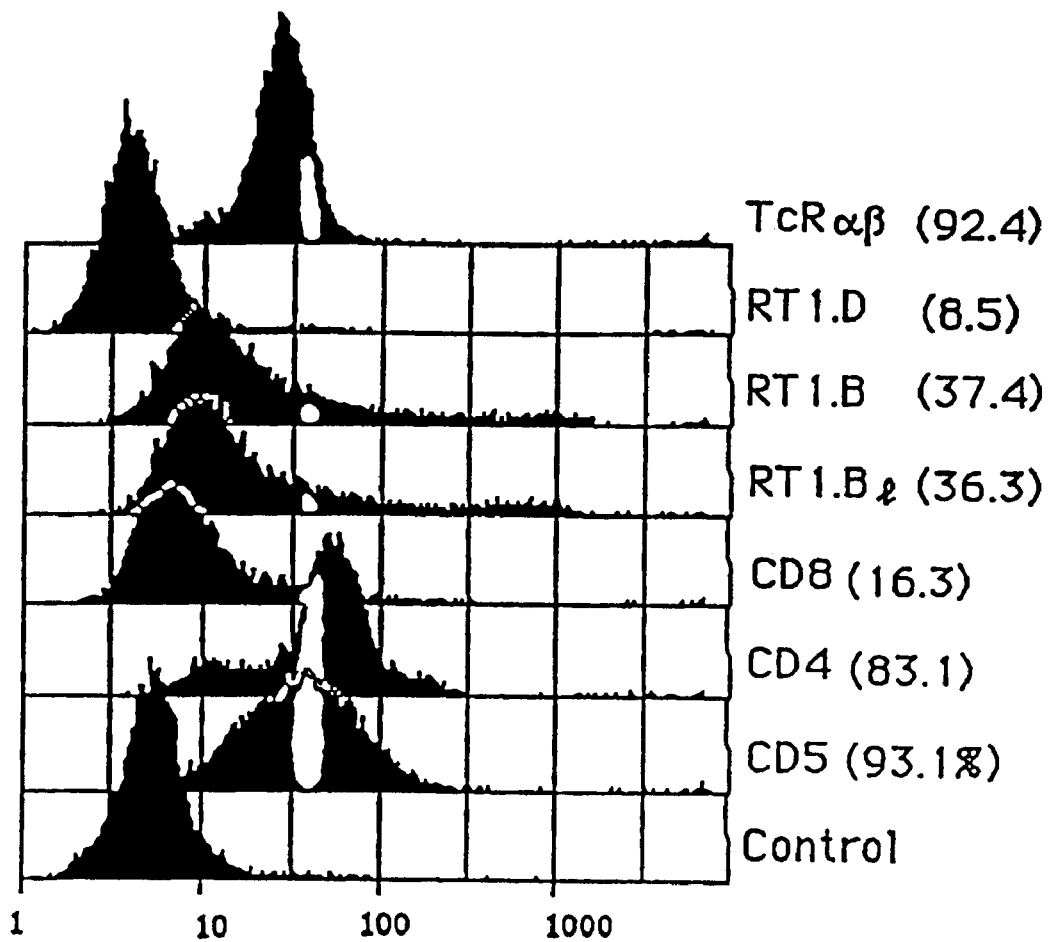
FIG. 3 is a flow cytometric profile of PI peptide-specific T cell line expression of cell surface antigens following 72 hour stimulation with concanavalin A. Histograms and percent positive expression for each primary antibody (in parentheses) were generated by FACScan analysis of 10,000 cells.

Cell surface antigen expression of the T cell lines was defined by flow cytometric analysis using a FACScan (Becton-Dickinson) and is shown in FIG. 3. PI-specific T line cells were positive for TcRαβ, were predominantly of the CD4$^+$/CD8$^-$ phenotype, and exhibited negligible expression of CD45RC (<1%). The cell surface phenotype exhibited by cells specific for GAD$_{412}$ and GAD$_{520}$ lines was similar. Depletion of the PI-specific T cell line of the small number of CD8$^+$ cells (using magnetic beads; DYNAL, Lake Success, N.Y.) neither abolished the ability of the remaining CD4$^+$/CD8$^-$ cells to respond vigorously to the PI peptide, nor inhibited the ability of the CD4$^+$ cells to adoptively transfer insulitis. Therefore, in DA(RP) rats, it appears that CD4$^+$ T cells specific for a peptide fragment of PI can mediate the adoptive transfer of insulitis, rather than T cells specific for comparable GAD peptides, even though all peptides result in vigorous, antigen-specific CD4$^+$ T cell proliferation.

In order to assess the persistence of antigen specificity of GAD- and PI-specific T cell lines in vivo, spleens were removed from rats injected with either GAD- or PI-specific T cells 18 days post-transfer. Splenocytes from rats injected with PI-specific cells exhibited the ability to respond specifically to PI peptide, but not GAD, as measured by $^3$H-Thymidine incorporation (anti-PI T cell line response to PI peptide stimulation index (S.I.)=41.9 vs. response to GAD=1.9). Similarly, splenocytes from rats injected with GAD-specific T cells were found to proliferate markedly to GAD peptide (S.I.=21.6) but not PI peptide (S.I.=1.3). Moreover, the islets of rats which received PI-specific T cells exhibited more severe insulitis at day +18 than at day +10 (63+10% involvement of islets). Pancreases from rats injected with GAD-specific T cells still showed no evidence of insulitis 18 days post-transfer.

Of particular interest is the finding that the pathogenic T cell epitope identified in proinsulin spans the endogenous cleavage site between the B-chain and C-peptide of insulin. Under normal enzymatic processing of proinsulin to the insulin B-chain and C-peptide, the exact area which contains the two overlapping binding motifs (as shown in Table I) is cleaved so that both motifs are destroyed (see FIG. 1). The aforementioned area of proinsulin would exist intact in significant quantities only in islet P-cells or in their vicinity where proinsulin is processed in an alternative manner. These results demonstrate that pathogenic T cell epitopes can be located in portions of molecules which are subsequently degraded during normal enzymatic processing. Since proinsulin is found in highest concentrations in the βcells of pancreatic islets, it is possible that this molecule, and not its individual degradation products (i.e., insulin and C-peptide) may serve as an autoantigen in the pathogenesis of Type I diabetes. Almost 99% of proinsulin is destined to become insulin via a regulated-release pathway from the P-cell granule, however, residual proinsulin travels in secretory vesicles along a constitutive release pathway (see Sizonenko, S. et al. (1991) Biochem. J. 278:621–625; Sizonenko, S. et al. (1993) Diabetes 42:933–936; Hutton, J. C. et al. (1989) Diabetologia 32:271–281; Halban, P. A. et al. (1991) Diabetologia 34:767–778). Of interest relative to the clinical onset of Type I diabetes is the finding that circulating proinsulin levels can be more than two times greater in recently diagnosed diabetics than in nondiabetics (Heaton, D. et al. (1988) Diabetologia 31:182–184; Heding, L. et al. (1981) Acta. Med. Scand. Suppl. 656:509).

In this example, it was possible to use both GAD and PI peptides to successfully generate peptide-specific T cell lines, the majority of which were CD4$^+$ and MHC Class II-restricted in recognition of their respective peptides in vitro. Both PI-specific and GAD-specific T cells were found to persist at least three weeks in the spleen following transfer and retain their antigen specificity. However, adoptive transfer experiments revealed that only PI-specific T cells were capable of mediating insulitis in vivo. Although splenocyte responses to GAD occur prior to detectable insulitis and suggest a role for GAD in the pathogenesis of autoimmune insulitis in NOD mice (see Kaufman, D. L. et al. (1993) Nature 366:69–72; Tisch, R. et al. (1993) Nature 366:72–75), the present studies found that rat T cells specific for selected GAD peptides do not produce islet lesions. The present study has identified another potentially significant autoantigen in addition to GAD by demonstrating that proinsulin-reactive T-cells are sufficient to yield insulitis. It has been shown that insulitis precedes diabetes by 2–3 weeks in BB rats (see Colle, E. (1990) Clin. Immunol. Immunopathol. 57:1–9). Given that circulating insulin levels in humans and mice with Type I diabetes are not significantly reduced until >95% of the islets are destroyed (Katz, J. D. et al. (1993) Cell 74:1089–1100), ongoing studies are monitoring insulitis and blood glucose levels for extended periods in rats given PI-specific T cells to determine if overt diabetes ensues as islets are increasingly involved by inflammatory cells.

EXAMPLE 2

Proinsulin Peptide-Specific T Cell Clones Induce Diabetes in BB Rats

In experiments similar to those described in Example 1, (Lewis×WF)F1, BB(DP) and BB(DR) rats were immunized for T cell line production to determine if the proinsulin peptide was also immunogenic in rats with RT1$^u$ haplotype. As in the RT1$^1$ rats described in Example 1, all RT1$^u$ and RT1$^{1/u}$ rats responded. Both the F1 hybrid, and BB(DR) rats produced a vigorous, antigen specific, predominantly CD4+ cell line against the proinsulin peptide. The BB(DP) responded in a specific manner. Anti-PI cells then were adoptively transferred to naive animals and the development of insulitis and full-blown diabetes in the animals was evaluated. Negative controls for the nonspecific, diabetogenic nature of the anti-PI cells included: BB(DR) rats given 30 million cells of a syngeneic cell line specific for myelin basic protein (which did not develop diabetes or EAE) and rats given similar number of T cells specific for GAD (which developed neither insulitis nor diabetes).

The results of these studies are summarized below in Table II.

TABLE II

| Rat Strain | RT-1 MHC type | Insulitis after anti-PI cell transfer | Diabetes after after anti-PI cells transfer |
|---|---|---|---|
| Lewis | A$^1$,B$^1$,D$^1$ | 0/10 | 0/10 |
| (Lew × WF)F1 | A$^{1/u}$,B$^{1/u}$,D$^{1/u}$ | 4/4 | 0/4 |
| DA(RP) | A$^u$,B$^1$,D$^1$ | 18/18* | 0/18 |
| BB(DR) | A$^u$,B$^u$,D$^u$ | 14/14 | 14/14 |

TABLE II-continued

| Rat Strain | RT-1 MHC type | Insulitis after anti-PI cell transfer | Diabetes after anti-PI cells transfer |
|---|---|---|---|
| BB(DP) | A$^u$,B$^u$,D$^u$ | 4/4 | 4/4 |
| (DA(RP) × BB(DR))F$_1$ | A$^{u/u}$,B$^{u/1}$,D$^{u/1}$ | 2/10 | 0/10 |

*in the(Lew × WF)F1 animals, insulitis involved under 20% of the islets ten days following transfer; in the DA(RP) over 40% of the islets were involved by insulitis ten days following transfer. All adoptive transfers employed between 20 to 30 million activated anti-PI cells injected intravenously.

Injection of the (Lewis×WF)FI anti-PI cell line into naive rats of the same F1 type produced a mild insulitis in some animals; but none became diabetic. However, adoptive transfer of the BB(DR) anti-PI cell line (and subsequently other anti-PI T cell lines derived similarly from BB(DR) rats) resulted in the development of overt insulin dependent diabetes mellitus in both BB(DR) or prediabetic BB(DP) rat. For both the BB(DP) and BB(DR) rats, cell transfer led to diabetes in only those getting anti-PI cells; litter mates given no cells, or infused with anti-GAD cells, remained normal for 30 days or more following the time of injections. Thus, this example demonstrates that the PI-specific T cells are sufficient to induce diabetes when transferred into genetically appropriate recipient animals.

EXAMPLE 3

Proinsulin Peptide-Reactive T Cells are Present in the Circulation of Type I Diabetic Humans In this example, peripheral blood from Type I diabetic and non-diabetic control individuals was studied to determine whether T cells reactive against human proinsulin peptide are present in diabetic individuals. Peripheral blood was obtained from Type I diabetics (n=9) and non-diabetic, age-matched controls (n=8). Lymphocytes were obtained by standard density centrifugation and cultured in the presence of human proinsulin peptide (10 µg/ml) or tetanus toxoid peptide (10 µg/ml). The amino acid sequences of the peptides were as follows:

specific proliferation assay was performed where T cell lines and clones were cultured with or without the appropriate peptide and irradiated, autologous leukocytes for 4.5 days, the last 12 hr including a pulse with $^3$H-thymidine. These data are summarized below in Table III.

TABLE III

| Subject | Sex | # PI Clones | PI. Stim Index | Max. CPM | TT Stim. Index |
|---|---|---|---|---|---|
| CONTROLS | | | | | |
| JR | F | 0 | 5.3 | 1,039 | 58.7 |
| KC | F | 0 | 12.8 | 4,264 | 13.9 |
| AG | F | 0 | 1.4 | 393 | 38.1 |
| RR | M | 3 | 11.8 | 4,093 | 21.6 |
| MF | M | 0 | 2.8 | 597 | 3.8 |
| CH | M | 0 | 1.0 | 470 | 8.3 |
| KW | M | 7 | 1.3 | 2,190 | 20.5 |
| MR | M | 0 | 4.3 | 928 | 155.8 |
| DIABETICS | | | | | |
| MW | F | 4 | 40.0 | 5,685 | 1.4 |
| BL | F | 3 | 3.5 | 1,918 | 8.3 |
| SJ | F | 3 | 5.5 | 712 | 2.0 |
| GG | M | 12 | 2.4 | 539 | 3.3 |
| TP | M | 11 | 16.9 | 4,864 | 19.1 |
| JW | M | 4 | 4.8 | 1,508 | 16.7 |
| WD | M | 16 | 17.6 | 21,336 | 4.8 |
| JS | M | 2 | 1.4 | 246 | 12.5 |
| TE | M | 3 | 5.8 | 1,733 | 8.3 |

As determined by $^3$H-thymidine uptake as a measure of antigen-specific proliferation, proinsulin-reactive T cell lines (8 of 9) and clones (9 of 9) (100%) were detected in Type I diabetic patients, whereas only 2 of 8 (25%) non-diabetic controls exhibited proinsulin-reactive T cells from peripheral blood. All subjects were found to have tetanus toxoid-reactive T cells as expected for a recall antigen response. Thus, this example demonstrates that proinsulin-reactive T cell lines and clones can be generated from the peripheral blood of human Type I diabetic patients, whereas such lines and clones are not readily generated from the peripheral blood of non-diabetic controls.

```
Human proinsulin      47G F F Y T P K T R R E A E D L Q V G64    (SEQ ID NO:4)

Tetanus toxoid        828L M Q Y I K A N S K F I G I T E L840    (SEQ ID NO:23)
```

To generate antigen-specific clones, 2×10$^5$ cells/well were cultured in 96-well plates, whereas to generate antigen-specific lines, 5×10$^6$ cells/well were cultured in 24-well plates, both for 10–14 days in medium containing autologous serum. The later 7–14 day culture period included supplementation with medium containing interleukin-2. At 14 days after the initiation of cell cultures, an antigen- Equivalents Those skilled in the art will recognize, or be able to ascertain using no more than routine experimentation, many equivalents to the specific embodiments of the invention described herein. Such equivalents are intended to be encompassed by the following claims.

What is claimed is:

1. A method useful in the diagnosis of Type-1 diabetes in a subject, comprising:
   a) obtaining a biological sample comprising T-cells from a subject;
   b) contacting a biological sample in vitro with a proinsulin peptide consisting of the sequence GFFYTPKTRREAEDLQVG (SEQ ID NO:4; and
   c) detecting the ability of the proinsulin peptide to preferentially stimulate the T-cells of diabetic subjects by measuring the ability of the T-cells to proliferate or ability of the T-cells to produce cytokines.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 330 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 1..330

(xi) SEQUENCE DESCRIPTION: SEQ ID NO:1:

```
AUG GCC CUG UGG AUG CGC CUC CUG CCC CUG CUG GCG CUG CUG GCC CUG    48
Met Ala Leu Trp Met Arg Leu Leu Pro Leu Leu Ala Leu Leu Ala Leu
 1               5                  10                  15

UGG GGA CCU GAC CCA GCC GCA GCC UUU GUG AAC CAA CAC CUG UGC GGC    96
Trp Gly Pro Asp Pro Ala Ala Ala Phe Val Asn Gln His Leu Cys Gly
            20                  25                  30

UCA CAC CUG GUG GAA GCU CUC UAC CUA GUG UGC GGG GAA CGA GGC UUC   144
Ser His Leu Val Glu Ala Leu Tyr Leu Val Cys Gly Glu Arg Gly Phe
        35                  40                  45

UUC UAC ACA CCC AAG ACC CGC CGG GAG GCA GAG GAC CUG CAG GUG GGG   192
Phe Tyr Thr Pro Lys Thr Arg Arg Glu Ala Glu Asp Leu Gln Val Gly
    50                  55                  60

CAG GUG GAG CUG GGC GGG GGC CCU GGU GCA GGC AGC CUG CAG CCC UUG   240
Gln Val Glu Leu Gly Gly Gly Pro Gly Ala Gly Ser Leu Gln Pro Leu
65                  70                  75                  80

GCC CUG GAG GGG UCC CUG CAG AAG CGU GGC AUU GUG GAA CAA UGC UGU   288
Ala Leu Glu Gly Ser Leu Gln Lys Arg Gly Ile Val Glu Gln Cys Cys
                85                  90                  95

ACC AGC AUC UGC UCC CUC UAC CAG CUG GAG AAC UAC UGC AAC           330
Thr Ser Ile Cys Ser Leu Tyr Gln Leu Glu Asn Tyr Cys Asn
            100                 105                 110
```

(2) INFORMATION FOR SEQ ID NO:2:

(i) SEQUENCE CHARACTERISTICS:
      (A) LENGTH: 110 amino acids
      (B) TYPE: amino acid
      (D) TOPOLOGY: linear (ii) MOLECULE TYPE: protein (xi) SEQUENCE DESCRIPTION: SEQ ID NO:2:

```
Met Ala Leu Trp Met Arg Leu Leu Pro Leu Leu Ala Leu Leu Ala Leu
 1               5                  10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80
```

```
Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

(2) INFORMATION FOR SEQ ID NO:3:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (v) FRAGMENT TYPE: internal (ix) FEATURE:
         (A) NAME/KEY: Modified-site
         (B) LOCATION: 1-15
         (D) OTHER INFORMATION: /note= "Xaa is any amino acid"

(ix) FEATURE:
         (A) NAME/KEY: Modified-site
         (B) LOCATION: 16
         (D) OTHER INFORMATION: /note= "Xaa is Ser or Thr"

(ix) FEATURE:
         (A) NAME/KEY: Modified-site
         (B) LOCATION: 19
         (D) OTHER INFORMATION: /note= "Xaa is Ser or Thr"

(ix) FEATURE:
         (A) NAME/KEY: Modified-site
         (B) LOCATION: 22
         (D) OTHER INFORMATION: /note= "Xaa is Glu or Asp"

(ix) FEATURE:
         (A) NAME/KEY: Modified-site
         (B) LOCATION: 23-37
         (D) OTHER INFORMATION: /note= "Xaa is any amino acid"

(xi) SEQUENCE DESCRIPTION: SEQ ID NO:3:

Xaa Xaa Xaa Xaa Xaa Xaa Xaa Xaa Xaa Xaa Xaa Xaa Xaa Xaa Xaa Xaa
1               5                   10                  15

Pro Lys Xaa Arg Arg Xaa Xaa Xaa Xaa Xaa Xaa Xaa Xaa Xaa Xaa Xaa
            20                  25                  30

Xaa Xaa Xaa Xaa Xaa
            35

(2) INFORMATION FOR SEQ ID NO:4:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (ix) FEATURE:
         (A) NAME/KEY: Modified-site
         (B) LOCATION: 5
         (D) OTHER INFORMATION: /note= "Xaa is Ser or Thr"

(ix) FEATURE:
         (A) NAME/KEY: Modified-site
         (B) LOCATION: 8
         (D) OTHER INFORMATION: /note= "Xaa is Ser or Thr"

(ix) FEATURE:
         (A) NAME/KEY: Modified-site
         (B) LOCATION: 11
```

(D) OTHER INFORMATION: /note= "Xaa is Glu or Asp"

(ix) FEATURE:
            (A) NAME/KEY: Modified-site
            (B) LOCATION: 14
            (D) OTHER INFORMATION: /note= "Xaa is Glu or Asp"

(xi) SEQUENCE DESCRIPTION: SEQ ID NO:4:

Gly Phe Phe Tyr Xaa Pro Lys Xaa Arg Arg Xaa Ala Glu Xaa Leu Gln
1               5                   10                  15

Val Gly (2) INFORMATION FOR SEQ ID NO:5:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (ix) FEATURE:
            (A) NAME/KEY: Modified-site
            (B) LOCATION: 5
            (D) OTHER INFORMATION: /note= "Xaa is Ser or Thr"

(ix) FEATURE:
            (A) NAME/KEY: Modified-site
            (B) LOCATION: 8
            (D) OTHER INFORMATION: /note= "Xaa is Ser or Thr"

(ix) FEATURE:
            (A) NAME/KEY: Modified-site
            (B) LOCATION: 11
            (D) OTHER INFORMATION: /note= "Xaa is Glu or Asp"

(ix) FEATURE:
            (A) NAME/KEY: Modified-site
            (B) LOCATION: 14
            (D) OTHER INFORMATION: /note= "Xaa is Glu or Asp"

(xi) SEQUENCE DESCRIPTION: SEQ ID NO:5:

Gly Phe Phe Tyr Xaa Pro Lys Xaa Arg Arg Xaa Val Glu Xaa Pro Gln
1               5                   10                  15

Val (2) INFORMATION FOR SEQ ID NO:6:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (ix) FEATURE:
            (A) NAME/KEY: Modified-site
            (B) LOCATION: 5
            (D) OTHER INFORMATION: /note= "Xaa is Ser or Thr"

(ix) FEATURE:
            (A) NAME/KEY: Modified-site
            (B) LOCATION: 8
            (D) OTHER INFORMATION: /note= "Xaa is Ser or Thr"

(ix) FEATURE:
            (A) NAME/KEY: Modified-site
            (B) LOCATION: 11
            (D) OTHER INFORMATION: /note= "Xaa is Glu or Asp"

```
        (ix) FEATURE:
              (A) NAME/KEY: Modified-site
              (B) LOCATION: 14
              (D) OTHER INFORMATION: /note= "Xaa is Glu or Asp"

(xi) SEQUENCE DESCRIPTION: SEQ ID NO:6:

Gly Phe Phe Tyr Xaa Pro Met Xaa Arg Arg Xaa Val Glu Xaa Pro Gln
1               5                  10                  15

Val (2) INFORMATION FOR SEQ ID NO:7:

(i) SEQUENCE CHARACTERISTICS:
              (A) LENGTH: 17 amino acids
              (B) TYPE: amino acid
              (D) TOPOLOGY: linear (ii) MOLECULE TYPE: peptide (v) FRAGMENT TYPE: internal (xi) SEQUENCE DESCRIPTION: SEQ ID NO:7:

Ala Ala Phe Tyr Ala Pro Lys Ser Arg Arg Glu Val Glu Asp Pro Ala
1               5                  10                  15

Ala (2) INFORMATION FOR SEQ ID NO:8:

(i) SEQUENCE CHARACTERISTICS:
              (A) LENGTH: 17 amino acids
              (B) TYPE: amino acid
              (D) TOPOLOGY: linear (ii) MOLECULE TYPE: peptide (v) FRAGMENT TYPE: internal (xi) SEQUENCE DESCRIPTION: SEQ ID NO:8:

Ala Ala Phe Tyr Thr Ala Lys Ser Arg Arg Glu Val Glu Asp Pro Ala
1               5                  10                  15

Ala (2) INFORMATION FOR SEQ ID NO:9:

(i) SEQUENCE CHARACTERISTICS:
              (A) LENGTH: 17 amino acids
              (B) TYPE: amino acid
              (D) TOPOLOGY: linear (ii) MOLECULE TYPE: peptide (v) FRAGMENT TYPE: internal (xi) SEQUENCE DESCRIPTION: SEQ ID NO:9:

Ala Ala Phe Tyr Thr Pro Ala Ser Arg Arg Glu Val Glu Asp Pro Ala
1               5                  10                  15

Ala (2) INFORMATION FOR SEQ ID NO:10:

(i) SEQUENCE CHARACTERISTICS:
              (A) LENGTH: 17 amino acids
              (B) TYPE: amino acid
              (D) TOPOLOGY: linear (ii) MOLECULE TYPE: peptide
```

(v) FRAGMENT TYPE: internal (xi) SEQUENCE DESCRIPTION: SEQ ID NO:10:

Ala Ala Phe Tyr Thr Pro Lys Ala Arg Arg Glu Val Glu Asp Pro Ala
1               5                   10                  15
Ala (2) INFORMATION FOR SEQ ID NO:11:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:11:

Ala Ala Phe Tyr Thr Pro Lys Ser Ala Arg Glu Val Glu Asp Pro Ala
1               5                   10                  15
Ala (2) INFORMATION FOR SEQ ID NO:12:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:12:

Ala Ala Phe Tyr Thr Pro Lys Ser Arg Ala Glu Val Glu Asp Pro Ala
1               5                   10                  15
Ala (2) INFORMATION FOR SEQ ID NO:13:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:13:

Ala Ala Phe Tyr Thr Pro Lys Ser Arg Arg Ala Val Glu Asp Pro Ala
1               5                   10                  15
Ala (2) INFORMATION FOR SEQ ID NO:14:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal

```
        (xi) SEQUENCE DESCRIPTION: SEQ ID NO:14:

Ala Ala Phe Tyr Thr Pro Lys Ser Arg Arg Glu Ala Glu Asp Pro Ala
1               5                  10                  15
Ala (2) INFORMATION FOR SEQ ID NO:15:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:15:

Ala Ala Phe Tyr Thr Pro Lys Ser Arg Arg Glu Val Ala Asp Pro Ala
1               5                  10                  15
Ala (2) INFORMATION FOR SEQ ID NO:16:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:16:

Ala Ala Phe Tyr Thr Pro Lys Ser Arg Arg Glu Val Glu Ala Pro Ala
1               5                  10                  15
Ala (2) INFORMATION FOR SEQ ID NO:17:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (v) FRAGMENT TYPE: internal (ix) FEATURE:
            (A) NAME/KEY: Modified-site
            (B) LOCATION: 1
            (D) OTHER INFORMATION: /note= "Xaa is Ser or Thr"

(ix) FEATURE:
            (A) NAME/KEY: Modified-site
            (B) LOCATION: 2-5
            (D) OTHER INFORMATION: /note= "Xaa is any amino acid"

(ix) FEATURE:
            (A) NAME/KEY: Modified-site
            (B) LOCATION: 7
            (D) OTHER INFORMATION: /note= "Xaa is Glu or Asp"

(xi) SEQUENCE DESCRIPTION: SEQ ID NO:17:

Xaa Xaa Xaa Xaa Xaa Xaa Xaa
1               5

(2) INFORMATION FOR SEQ ID NO:18:
```

```
        (i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:18:

Gly Phe Phe Tyr Ala Pro Lys Ser Arg Arg Ala Val Glu Asp Pro Gln
1               5                  10                  15
Val (2) INFORMATION FOR SEQ ID NO:19:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:19:

Gly Phe Phe Tyr Thr Pro Lys Ala Arg Arg Glu Val Glu Ala Pro Gln
1               5                  10                  15
Val (2) INFORMATION FOR SEQ ID NO:20:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:20:

Ala Ala Ala Ala Thr Ala Ala Ser Ala Ala Glu Ala Ala Asp Ala Ala
1               5                  10                  15
Ala (2) INFORMATION FOR SEQ ID NO:21:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:21:

Leu Leu Gln Cys Ser Ala Ile Leu Val Lys Glu Lys Gly Ile Leu Gln
1               5                  10                  15
Gly (2) INFORMATION FOR SEQ ID NO:22:

(i) SEQUENCE CHARACTERISTICS:
            (A) LENGTH: 17 amino acids
```

```
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:22:

Tyr Ile Pro Gln Ser Leu Arg Gly Val Pro Asp Ser Pro Glu Arg Arg
1               5                   10                  15

Glu (2) INFORMATION FOR SEQ ID NO:23:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:23:

Leu Met Gln Tyr Ile Lys Ala Asn Ser Lys Phe Ile Gly Ile Thr Glu
1               5                   10                  15

Leu
```